(12) United States Patent
Kiessling et al.

(10) Patent No.: US 7,807,140 B2
(45) Date of Patent: Oct. 5, 2010

(54) MAGNETIC RESONANCE IMAGING CONTRAST AGENTS SYNTHESIZED USING RING-OPENING METATHESIS POLYMERIZATION

(75) Inventors: Laura L. Kiessling, Madison, WI (US); Ronald T. Raines, Madison, WI (US); Matthew J. Allen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 159 days.

(21) Appl. No.: 11/743,740

(22) Filed: May 3, 2007

(65) Prior Publication Data

US 2008/0063602 A1    Mar. 13, 2008

Related U.S. Application Data

(60) Provisional application No. 60/746,285, filed on May 3, 2006.

(51) Int. Cl.
*A61B 5/055* (2006.01)
(52) U.S. Cl. .................. 424/9.365; 424/1.11; 424/1.53; 424/1.65; 424/9.1; 424/9.36; 534/10; 534/11; 534/12; 534/15
(58) Field of Classification Search ................ 424/1.11, 424/1.65, 9.1, 9.3, 9.31, 9.32, 9.321, 9.322, 424/9.323, 9.33, 9.34, 9.341, 9.35, 9.351, 424/9.36, 9.361, 9.363, 1.53, 9.365; 534/7, 534/10–16
See application file for complete search history.

(56) References Cited

U.S. PATENT DOCUMENTS

| 5,756,688 | A | 5/1998 | Snow et al. |
| 5,880,231 | A | 3/1999 | Grubbs et al. |
| 6,271,315 | B1 | 8/2001 | Kiessling et al. |
| 6,291,616 | B1 | 9/2001 | Kiessling et al. |
| 2004/0248801 | A1 * | 12/2004 | Kiessling et al. ............ 514/12 |
| 2005/0008570 | A1 | 1/2005 | Raymond et al. |

FOREIGN PATENT DOCUMENTS

WO    WO 01/71309    9/2001

OTHER PUBLICATIONS

International Search Report, Corresponding to International Application No. PCT/US07/68099, Mailed Sep. 3, 2008.
Written Opinion, Corresponding to International Application No. PCT/US07/68099, Mailed Sep. 3, 2008.
International Preliminary Report on Patentability, International Application No. PCT/US2007/068099, 6 pages, (2007).
Aime et al. (2005) "Gd(III)-Based Contrast Agents for MRI," *Inorg. Chem.* 57:173-237.
Aime et al. (2001) "Protein-Bound Metal Chelates," In; *The Chemistry of Contrast Agents in Medical Magnetic Resonance Imaging*, Merbach et al. eds., John Wiley & Sons, Ltd., New York, pp. 193-241.
Allen et al. (2004) "Magnetic Resonance Contrast Agents for Medical and Molecular Imaging," *J. Met. Ions Biol. Syst.* 42:1-38.
Allen et al. (2006) "Contrast Agents for Magnetic Resonance Imaging Synthesized with Ring-Opening Metathesis Polymerization," *J. Am. Chem. Soc.* 128(20):6534-6536.
Anelli et al. (2001) "Synthesis of MRI Contrast Agents I. Acrylic Ligands," In; *The Chemistry of Contrast Agents in Medical Magnetic Resonance Imaging*, Merbach et al. eds., John Wiley & Sons, Ltd., New York, pp. 121-155.
Brigger et al. (2002) "Nanoparticles in Cancer Therapy and Diagnosis," *Adv. Drug Deliv. Rev.* 54:631-651.
Caravan et al. (1999) "Gadolinium(III) Chelates as MRI Contrast Agents: Structure, Dynamics, and Applications," *Chem. Rev.* 99:2293-2352.
Doble et al. ( 2003) "Toward Optimized High-Relaxivity MRI Agebnts: The Effect of Ligand Basicity on the Thermodynamic Stability of Hexadentate Hydroxypyridonate//Catecholate Gadolinium(III) Complexes," *Inorg. Chem.* 42:4930-4937.
Feutrill et al. (1970) "Demethylation of Aryl Methyl Ethers with Thioethoxide Ion in Dimethyl Formamide," *Tetrahedron Lett.* 16:1327-1328.
Holmes et al. (1984) "Solution Characterization of Carboxybenzoquinone and the Isolation of Derived Quinhydrones," *J. Org. Chem.* 49:4736-4738.
Jacques et al. (2001) "Synthesis of MRI Contrast Agents II. Macrocyclic Ligands," In; *The Chemistry of Contrast Agents in Medical Magnetic Resonance Imaging*, Merbach et al. eds., John Wiley & Sons, Ltd., New York, pp. 157-191.
Love et al. (2002) "A Practical and Highly Active Ruthenium-Based Catalyst that Effects the Cross Metathesis of Acrylonitrile," *Angew Chem. Int Ed.* 41:4035-4037.
Pierre et al. (2005) "Dendrimeric Gadolinium Chelate with Fast Water Exchange and High Relaxivity at High Magnetic Field Strength," *J. Am. Chem. Soc.* 127:504-505.
Pontrello et al. (2005) Solid-Phase Synthesis of Polymers Using the Ring-Opening Metathesis Polymerization *J. Am. Chem. Soc.* 127:14536-14537.
Raymond et al. (2005) "Next Generation, High Relaxivity Gadolinium MRI Agents," *Bioconjug. Chem.* 16:3-8.

(Continued)

*Primary Examiner*—D L Jones
(74) *Attorney, Agent, or Firm*—Greenlee Sullivan P.C.

(57) ABSTRACT

Polymeric chelating agents and metal chelates, particularly those of lanthanide metals and more specifically those of Gd(III), useful as contrast agents in magnetic resonance imaging (MRI) for therapeutic and diagnostic applications as well as clinical and biomedical research applications. The polymeric chelates are generated using ring-opening metathesis polymerization (ROMP). Polymers can have multiple sites for functionalization allowing for the synthesis of multimodal and targeted contrast agents. Hydroxypyridonate (HOPO)-based chelating moieties are integrated into a ROMP-derived polymer. More specifically, the HOPO-based chelating moiety is integrated into a benzonorbornadiene unit that constitutes the backbone of the polymer. The ROMP-derived polymer chelators can comprise multiple metal ions, particularly Gd(III) ions, in polymers of varying lengths to provide a series of agents with controlled relaxivites. Polymer chelates include those that are water-soluble.

41 Claims, 1 Drawing Sheet

OTHER PUBLICATIONS

Reichert et al. (1999) "Metal Complexes as Diagnostic Tools," *Coord. Chem. Rev.* 184:3-66.

Strong et al. (1999) "A General Synthetic Route to Defined, Biologically Active Multivalent Arrays," *J. Am. Chem. Soc.* 121:6193-6196.

Trnka et al. (2001) "The Development of $L_2X_2Ru$=CHR Olefin Metathesis Catalysts: An Organometallic Success Story," *Acc. Chem. Res.* 34:18-29.

Troth et al. (1999) "Gd(DTPA-bisamide)alkyl Copolymers: A Hint for the Formation of MRI Contrast Agents with Very High Relaxivity," *Chem. Eur. J.* 5(4):1202-1211.

Tweedle et al. (1999) "Magnetic Resonance Imaging (MRI) Contrast Agents," *Top. Biol. Inorg. Chem.* 2:1-43.

Uzgiris et al. (2004) "Conformation and Structure of Polymeric Contrast Agents for Medicinal Imagin," *Biomacromolecules* 5:54-61.

Xu et al. (2004) "Gadolinium(III) 1,2-Hydroxypyridonate-Based Complexes: Toward MRI Contrast Agents of High Relaxivity," *Inorg. Chem.* 43:5492-5494.

Xu et al. (1995) "Gadolinium Complex of Tris[(3-hydroxyl-1-methyl-2-oxo-1,2-didehydropyridine-4-carboxamido)ethyl]-amine: A New Class of Gadolinium Magnetic Resonance Relaxation Agents," *J. Am. Chem. Soc.* 117:7245-7246.

* cited by examiner

MAGNETIC RESONANCE IMAGING CONTRAST AGENTS SYNTHESIZED USING RING-OPENING METATHESIS POLYMERIZATION

CROSS-REFERENCE TO RELATED APPLICATIONS

This application claims the benefit of U.S. Provisional Patent Application 60/746,285, filed May 3, 2006, which is incorporated by reference herein in its entirety.

STATEMENT REGARDING UNITED STATES GOVERNMENT FUNDING

This invention was made under funding from the United States government through the National Institutes of Health grant numbers GM49975 and GM44783. The U.S. government has certain rights in this invention.

BACKGROUND OF THE INVENTION

Magnetic Resonance Imaging (MRI) is a powerful diagnostic method in which three-dimensional images in vivo of body tissues are obtained based on the distribution of water in these tissues. MRI contrast agents administered prior to imaging alter the relaxation times of protons in their vicinity enhancing specific features of an image. MRI contrast agents improve the sensitivity and utility of MRI diagnostics. See: The Chemistry of Contrast Agents in Medical Magnetic Resonance Imaging; Merbach, A. E., Toth, E., Eds.; John Wiley & Sons, Ltd.: New York, 2001; Tweedle, M. F.; Kumar, K. *Top. Biol. Inorg. Chem.* 1999, 2, 1-43; Reichert, D. E.; Lewis, J. S.; Anderson, C. J. *Coord. Chem. Rev.* 1999, 184, 3-66; and Allen, M. J.; Meade, T. J. *Met. Ions Biol. Syst.* 2004, 42, 1-38.

Raymond and coworkers have reported hydroxypyridonate (HOPO)-based Gd(III) chelates that are more effective at enhancing the contrast of MR images (Raymond, K. N.; Pierre, V. C. Bioconjugate Chem. 2005, 16, 3-8. and Xu, J.; Franklin, S. J.; Whisenhunt, D. W., Jr.; Raymond, K. N. J. Am. Chem. Soc. 1995, 117, 7245-7246. U.S. published patent application 2005/0008570 (Raymond et al.), published Jan. 13, 2005, reports hydroxypyridonate and hydroxypyrimidinone chelating agents including Gd(III) complexes for use as MRI contrast agents.

The strength of Gd(III)-based contrast agents can be improved by increasing the number of coordinated water molecules, optimizing the water exchange rate between bound and bulk water molecules, increasing the rotational correlation time, or increasing the number of Gd(III) ions per molecule (Caravan, P.; Ellison, J. J.; McMurry, T. J.; Lauffer, R. B. *Chem. Rev.* 1999, 99, 2293-2352; Uzgiris, E. E.; Cline, H.; Moasser, B.; Grimmond, B.; Amaratunga, M.; Smith, J. F.; Goddard, G. *Biomacromolecules* 2004, 5, 54-61; Aime, S.; Botta, M.; Terreno, E. *Adv. Inorg. Chem.* 2005, 57, 173-237.) The HOPO-based agents have an increased number of water molecules in the innersphere environment and a near optimal water exchange rate; together, these features lead to a higher relaxivity (Xu, J.; Franklin, S. J.; Whisenhunt, D. W., Jr.; Raymond, K. N. *J. Am. Chem. Soc.* 1995, 117, 7245-7246.) Increasing the rotational correlation time can further improve these agents (Pierre, V. C.; Botta, M.; Raymond, K. N. *J. Am. Chem. Soc.* 2005, 127, 504-505.)

This invention relates to polymeric HOPO-based metal chelating agents and metal chelates generated by using ring-opening metathesis polymerization (ROMP). Multiple HOPO-based chelating groups are integrated into structural units that constitute the backbone of the polymer formed upon ROMP. Using this technique highly sensitive and tunable contrast agents can be made through incorporation of multiple HOPO-based Gd(III) chelates into an easily functionalizable macromolecule.

Polymers comprising one or more Gd(III) complexes have been made which function as MRI contrast agents with extraordinary sensitivity and versatility. Additionally, the utility of contrast agents can be increased by equipping them with targeting moieties or fluorescent probes.

ROMP is an ideal polymerization method for this purpose because it can yield polymers of well-defined length. See: Trnka, T. M.; Grubbs, R. H. Acc. Chem. Res. 2001, 34, 18-29 and U.S. Pat. No. 5,880,231 (Grubbs et al.). Additionally, ROMP is amenable to the generation of polymers with multiple sites for functionalization, allowing for the synthesis of multimodal and targeted contrast agents. See: Strong, L. E.; Kiessling, L. L. J. Am. Chem. Soc. 1999, 121, 6193-6196 and Pontrello, J. K.; Allen, M. J.; Underbakke, E. S.; Kiessling, L. L. J. Am. Chem. Soc. 2005, 127, 14536-14537; U.S. Pat. No. 6,291,616 (Kiessling et al.); International published application WO01/71309 (Kiessling et al.). U.S. Pat. No. 6,271,315 (Kiessling et al.) relates to methods for making ROMP-derived polymers employing functionalized carbene catalysts and/or functionalized capping agents.

SUMMARY OF THE INVENTION

This invention is related to polymeric metal chelates, particularly those of lanthanide metals and in one specific embodiment, those of Gd(III), which are useful as contrast agents in magnetic resonance imaging (MRI) for therapeutic and diagnostic applications as well as clinical and biomedical research applications. The polymeric chelates of this invention are generated using ring-opening metathesis polymerization (ROMP). ROMP can be used to generate polymers with multiple sites for functionalization allowing for the synthesis of multimodal and targeted contrast agents. Hydroxypyridonate (HOPO)-based chelating moieties are integrated into a ROMP-derived polymer. More specifically, the HOPO-based chelating moiety is integrated into a benzonorbornadiene unit that constitutes the backbone of the polymer. The ROMP-derived polymer chelators of this invention comprise multiple metal ions, particularly Gd(III) ions, in polymers of varying lengths to provide a series of agents with controlled relaxivities. Preferred polymer chelates of this invention are water-soluble. The ROMP-derived polymer chelators of this invention also comprise graft block co-polymers in which at least one block carries one or more chelating moieties, particularly HOPO-based chelating moieties.

Polymer chelating agents and metal chelates of this invention have the formula:

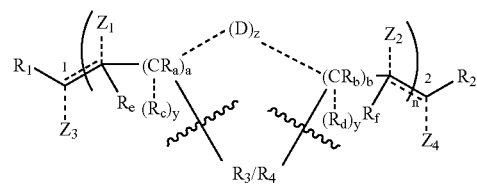

Formula 1 and salts thereof, where:

n indicates the average number of repeating units in the polymer;

z is 1 or 0 to indicate the presence or absence of D (where dotted lines indicate bonds to D, if present);

y is 1 or 0 to indicate the presence or absence of $R_c$ or $R_d$, where dotted lines indicate bonds to these groups, if present;

a and b are, independently, 0, 1 or 2:

D, if present, is selected from $C(R_a)_2$, O, S, $NR_N$, and $NCOR_N$;

$R_a$, $R_b$, $R_e$, $R_f$ and $R_c$ and $R_d$, if present, are, independently, H or alkyl groups having 1 to 3 carbon atoms;

$Z_1$-$Z_4$, independently, are H or hydroxide groups or are not present, where dashed lines indicate bonds to $Z_1$-$Z_4$, if present;

dashed lines at bonds 1 and 2 indicate that these bonds may be double or single bonds, when $Z_1$ and $Z_3$ are present bond 1 is a single bond, when $Z_2$ and $Z_4$ are present bond 2 is a single bond;

$R_1$ and $R_2$ are selected from H, aryl, ketone groups, aldehyde groups, or an -$L_4$-$R_{10}$ group where $R_{10}$ is selected from a reactive functional group, a targeting group, a macromolecule, a particle, particularly a nanoparticle, a solid (e.g., the surface of a solid, such as a bead) or a labeling group and $L_4$ is a linker, more specifically one of $R_1$ or $R_2$ can be a group that is derived from the ruthenium ROMP reaction initiator and one of $R_1$ or $R_2$ can be derived from the ketone or aldehyde functional group in an electron-rich terminator for the ROMP reaction;

$R_N$ is selected from hydrogen, alkyl, alkenyl, alkynyl, ether, amine, amide, ester or aryl groups wherein one or more carbons of these groups may be substituted with one or more halides, hydroxides, alkyl, alkoxide, aryl or aryloxide groups;

$R_3$ is a metal chelating group with or without a metal ion chelated in the chelating group; and $R_4$ is a group other than a chelating group which can include a spacer group, a reactive group, a targeting group, a solubilizing group, a labeling group, and/or groups that increase the rotation correlation time of the polymers, and in a specific embodiment $R_4$ is a ROMP monomer group ($R_M$) or a ROMP-derived polymer side branch formed by ROMP from the monomer attached to the main ROMP-derived polymer chain.

An individual $R_4$ group may have two or more functions as listed. For example $R_4$ groups carrying guanidinium moieties can function as spacers and as solubilizing groups.

Polymers of Formula 1 where $R_4$ is $R_M$ are precursors to metal chelating ROMP-derived graft copolymers. In another specific embodiment, precursors of metal chelating polymers are ROMP-derived polymers of Formula 1 carrying at least one $R_M$ (preferably not at an end of the ROMP-derived polymer) and carrying at least one $R_3$ group which is an $R_3'$ group, where $R_3'$ is a group that is a chemical precursor of the $R_3$ metal chelating moiety, which can be converted into the metal chelating moiety. In yet another specific embodiment, precursors of metal chelating ROMP-derived graft copolymer are graft co-polymers of Formula 1 where $R_3$ is $R_3'$ and $R_4$ is $R_M$ or is the ROMP-derived polymer side branch formed from $R_M$ by ROMP. In specific embodiments, $R_3'$ is a group that comprises an activated ester which can be reacted with selected reagents to form the desired metal chelating moiety. $R_M$ is in general any group containing a cyclic olefin, particularly a strained cyclic olefin, that reacts in the presence of one or more than one different free ROMP monomers by ring-opening polymerization to form a ROMP-derived polymer side branch attached to the main ROMP-derived polymer chain. Precursors of metal chelating graft copolymers include linear chain ROMP-derived polymers of Formula 1 carrying at least one $R_3'$ group and at least one $R_M$ group, graft copolymers having at least one $R_3'$ group and at least one ROMP-derived side-chain polymers (preferably not at a ROMP-derived polymer end) linear ROMP-derived polymers carrying at least one $R_3$ metal chelating moiety and one or more $R_M$ groups. In each case, the precursor can carry a number of other $R_4$ groups which may be the same or different, which function as spacers, additional reactive groups, targeting groups, solubilizing groups, and labeling groups. In specific embodiments, metal chelating groups can be incorporated in the main ROMP-derived chain as well as in the side-chain ROMP-derived polymers. In specific embodiments, metal chelating groups are incorporated into the only the main ROMP-derived chain.

In a related embodiment, metal chelating graft copolymers in which the metal chelating groups are carried in the ROMP-derived side-chain polymers may be formed from a linear chain ROMP-derived polymer, which carries one or more $R_M$ groups, but no $R_3$ or $R_3'$ groups. One or more $R_3'$ groups are then introduced into the copolymer during polymerization of the ROMP-derived side-chain polymers by addition of ROMP monomers carrying a group which can react to form the desired metal chelating moiety.

In specific embodiments, up to 50% of the total available sites are ROMP-derived side-chain polymers. In specific embodiments, the number of graft chains is from 8 to 15 monomers long, providing from 1-7 side chains. Other specific embodiments are described below. In a specific embodiment, metal chelating groups can be incorporated into the side chains, as is described for the main chain. For embodiments having side chains, any monomer can be used to form the side chains, including those shown below and described herein, as well as conventional MRI monomers, or any strained olefin having functional groups that are compatible with the polymerization conditions (for example, alkyl, aryl, alkoxy, aryloxyl, ketone, a positively charged group, a negatively charged group, or a reactive functional group attached via a linker, as further described herein). In addition, monomers can be modified to produce the structures shown in Formulas 2, 2A, 2B, 3, 3A or 3B below, as known in the art. No crosslinking is seen using the monomers shown in the Schemes below, particularly Scheme 3.

Example Monomers:

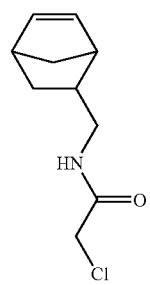

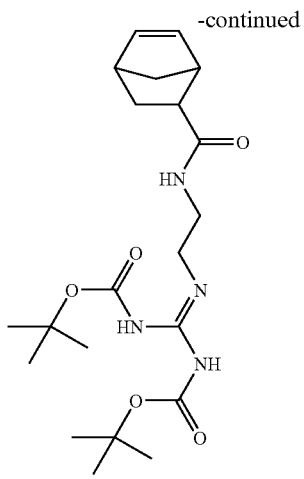

Each repeating unit of the polymer contains either an $R_3$ or an $R_4$ group. In specific embodiments, the polymer contains at least one $R_3$ group and preferably contains two or more $R_3$ groups. In specific embodiments, a polymer contains one or more $R_3$ groups, in combination with one or more $R_4$ groups which are spacers or solubilizing groups and in further combination with one or more $R_4$ groups that are targeting groups.

In the formulas herein a wavy line employed as a bond or displayed perpendicular to a bond indicates the point or points at which the displayed moiety (e.g., $R_1$, $R_3$, etc.) is attached to the remainder of the molecule. As is conventional, the use of wavy lines as bonds indicates that alternative isomers and stereoisomers are included in the structure.

Polymers in general can be any length, but preferably are sufficiently short that they exhibit some measurable level of water-solubility. The water-solubility of a given polymer can be enhanced by the introduction of $R_4$ groups which are solubilizing groups. In general, the polymers herein contain two or more different monomer units and as such are copolymers. The integer "n" represents the average number of monomer units in the polymer and is essentially equivalent to the degree of polymerization (DP). The different monomers can be randomly linked to one another in the polymers of this invention. Alternatively, blocks of the same monomer may be linked to one another to form a portion of a polymer (i.e., block polymers).

A polymer may contain more than one $R_3$ groups that are different and may contain more than one $R_4$ groups that are different.

$L_4$ are linker groups that function to attach a selected chemical species (e.g., a targeting group) or a particle or a solid to the metal chelate. $L_4$ can be any diradical comprising two or more carbon atoms, including, among others, alkylene, alkenylene, and alkynylene diradicals, where one or more —$CH_2$— can be replaced with —O—, —$NR_N$—, —CO—, —COO—, or —$CONR_N$—, and wherein carbons can be optionally substituted with one or two halides, hydroxides, alkyl, alkoxide, aryl or aryloxide groups. $L_4$ can be a cleavable linker that can be selectively cleaved by exposure to a chemical compound (e.g., a reagent), a biological molecule (e.g., an enzyme), or to a medium or stimulus that can effect bond cleavage (e.g., a change in pH or exposure to light of a selected wavelength).

In specific embodiments, the metal chelates and chelating agents of this invention are linked to a reactive functional group, a targeting group, a macromolecule, a particle, particularly a nanoparticle, a solid (e.g., the surface of a solid, such as a bead) or a labeling group. In specific embodiments, the reactive functional group, targeting group, macromolecule, particle, particularly a nanoparticle, solid (e.g., the surface of a solid, such as a bead) or labeling group is attached to the polymer backbone and particularly is attached at $R_2$. In other embodiments, the reactive functional group, targeting group, macromolecule, particle, particularly a nanoparticle, solid (e.g., the surface of a solid, such as a bead) or labeling group is attached to the polymer backbone via linkage to a monomer as $R_4$.

In specific embodiments, the polymeric chelating agents and metal chelates of this invention have the formula:

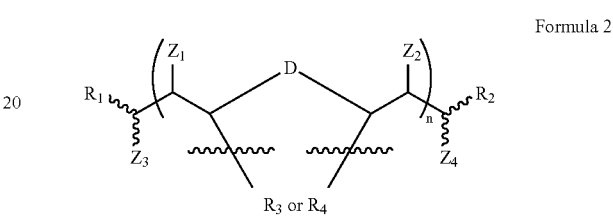

Formula 2 where z is 1, a and b are both 1, y is 0, and $R_a$, $R_b$, $R_e$ and $R_f$ are hydrogens and other variables are as defined above.

In other specific embodiments, the polymeric chelating agents and metal chelates of this invention have the formula:

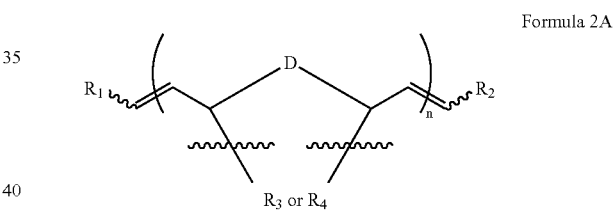

Formula 2A where n, D, $R_1$-$R_4$ are as defined above.

In further specific embodiments the polymeric chelating agents and metal chelates of this invention have the formula:

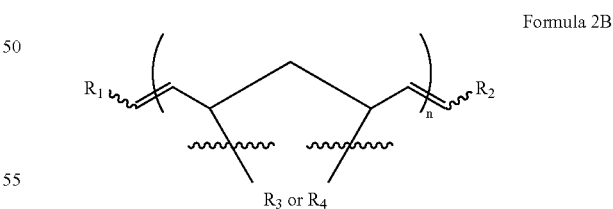

Formula 2B where n, $R_1$-$R_4$ are as defined above.

In specific embodiments, $R_1$ and $R_2$ in the above formulas are, independently, selected from phenyl rings, optionally substituted with one or more halides or one or more, hydroxide, alkyl, or alkoxy groups, ketones, aldehdyes, esters or activated ester groups.

The polymeric chelating agents and metal chelates of this invention also include those having the formula:

Formula 3

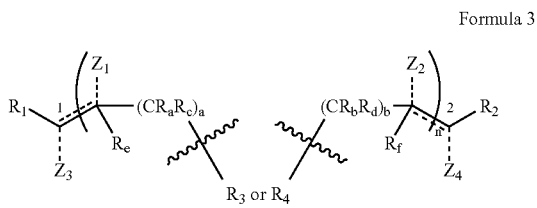

where a and b are, independently, 1 or 2, and n, $Z_1$-$Z_4$, $R_1$-$R_4$, $R_a$, $R_b$, $R_c$, $R_d$, $R_e$ and $R_f$ are as defined above and bonds 1 and 2 can be single or double bonds as described above.

Polymeric chelating agents and metal chelates of this invention further include those having formulas:

Formula 3A

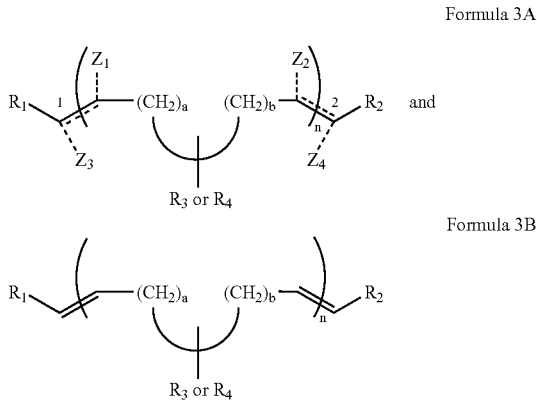

and

Formula 3B where a and b are, independently, 1 or 2, and n, $Z_1$-$Z_4$, and $R_1$-$R_4$, are as defined above and bonds 1 and 2 can be single or double bonds as described above.

For each of Formulas 1, 2, 2A, 2B, 3, 3A and 3B above, $R_3$ can be selected to be metal chelating group having the formula:

Formula $R_3$-1

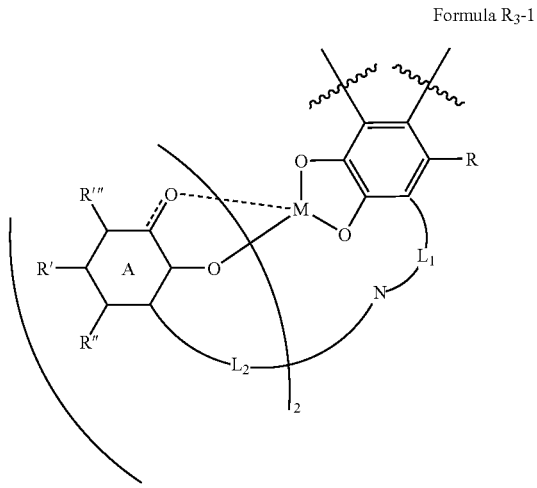

wherein:

M is a metal ion, in particular, a transition metal, an actinide metal, a lanthanide metal, particularly a metal in the +3 oxidation state and more specifically Gd(III);

R, R', R" and R''', independently, are selected from the group consisting of hydrogen or halide atoms and alkyl, alkenyl, alkynyl, aryl, alkoxy, aryloxy, thioalkoxyl, ether, thioether, heterocyclic, hydroxide, carboxyl, ester, amino, or amide groups, each of which is, if possible, optionally substituted. Possible substituents include one or more halogens, one or more amine groups, one or more hydroxide groups, one or more alkyl, alkenyl, alkynyl, aryl, alkoxyl or aryloxy groups;

$L_1$ and $L_2$ are linking groups, where two $L_2$ groups and one $L_1$ group are bonded to the N as indicated, where these groups, independently of other $L_1$ and $L_2$ groups, can be any diradical comprising two or more carbon atoms, including, among others, alkylene, alkenylene, and alkynylene diradicals where one or more —CH$_2$— are replaced with —O—, —NR$_N$—, —CO—, —COO—, or —CONR$_N$—, and wherein carbons can be optionally substituted, for example, with one or two halides, hydroxides, alkyl, alkoxide, aryl or aryloxide groups;

$R_N$ is selected from hydrogen, alkyl, alkenyl, alkynyl, ether, amine, amide, ester or aryl groups wherein one or more carbons of these groups are optionally substituted, for example, with one or more halides, azides, thioethers, hydroxides, alkyl, alkoxide, heterocyclic, aryl or aryloxide groups; and the two six-member rings A, independent of each other, can be selected from the group consisting of nitrogen-containing rings A1, A2 and A3, respectively:

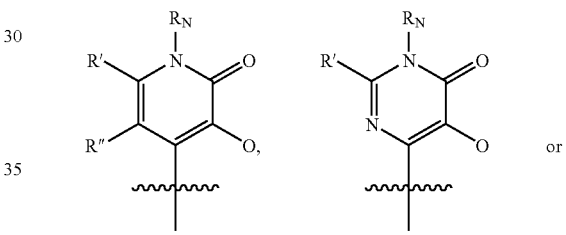

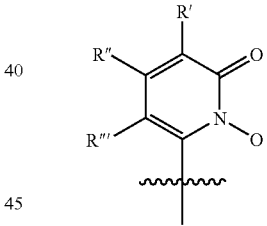

or and ring A4:

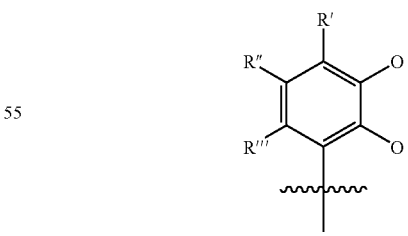

The dashed line in the generic A ring above between the oxygen and the ring carbon indications the presence of a bond, dependent upon the structure of the A ring.

In preferred embodiments of the metal chelating polymers herein at least one of the two six-member rings of the $R_3$ group is a nitrogen-containing ring. The two A rings can be the same or different. Both A rings may be nitrogen-containing rings. In a specific embodiment, both A rings are ring A1.

For each of Formulas 1, 2, 2A, 2B, 3, 3A and 3B above, $R_4$ can be selected to be a spacer group having the formula:

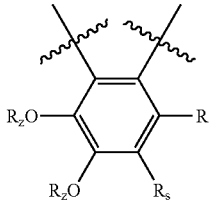

where $R_z$ is selected from a hydrogen atom, a protecting group that can be removed or a small alkyl group; and $R_s$ is selected from alkyl, alkenyl, alkynyl, aryl, alkoxy, aryloxy, thioalkoxyl, ether, thioether, heterocyclic in which one or more non-neighboring carbons can be replaced with —O—, —S—, —NR$_N$—, —CO—, —COO—, or —CONR$_N$— and which are optionally substituted with one or more halogens, one or more amine groups, one or more hydroxide groups, one or more alkyl, alkenyl, alkynyl, aryl, alkoxyl or aryloxy groups and/or one or more charged groups, including among others, —N$^+$(R$_N$)$_3$, —NH—C(=NH$_2$)$^+$—NH$_2$; and —COO$^-$ and salts thereof. $R_s$ can also be selected to be an -L$_3$-R$_5$ where L$_3$ is a linker group and in specific embodiments R$_5$ of a portion of the R$_4$ groups in the metal chelates or chelating agents can be selected from a reactive functional group, a targeting group, a macromolecule, a particle, particularly a nanoparticle, a solid (e.g., the surface of a solid, such as a bead) or a labeling group. In specific embodiments only one or two of the R$_4$ groups of the polymer have R$_5$ that is a reactive functional group, a targeting group, a macromolecule, a particle, particularly a nanoparticle, a solid (e.g., the surface of a solid, such as a bead) or a labeling group.

L$_3$ are linker groups that function to attach a selected chemical species (e.g., a targeting group) or a particle or a solid to the metal chelate. L$_3$ can be any diradical comprising two or more carbon atoms, including, among others, alkylene, alkenylene, and alkynylene diradicals, where one or more —CH$_2$— are replaced with —O—, —NR$_N$—, —CO—, —COO—, or —CONR$_N$—, and wherein carbons can be optionally substituted, for example, with one or two halides, hydroxides, alkyl, alkoxide, aryl or aryloxide groups. L$_3$ can be a cleavable linker that can be selectively cleaved by exposure to a chemical compound (e.g., a reagent), to a biological molecules (e.g., an enzyme) or to a medium or stimulus that can effect bond cleavage (e.g., a change in pH or exposure to light of a selected wavelength).

In preferred embodiments, not all of the monomers of the polymers of this invention carry chelating groups (R$_3$). In specific embodiments, the ratio of spacer or solubilizing groups to chelating groups ranges from 10:1 to 1:2. In more specific embodiments, the ratio of spacer or solubilizing groups to chelating groups ranges from 10:1 to 1:1. In other embodiments, this ratio ranges from 5:1 to 2:1. In other embodiments, this ratio is about 3:1 or 4:1. In specific embodiments, polymers of this invention carry 1 to 5 targeting or labeling groups in addition to R$_3$ and other R$_4$ groups. In preferred embodiments, polymers of this invention carry one or two targeting or labeling groups in addition to R$_3$ and other R$_4$ groups. In preferred embodiments, polymers herein carry 1-10 R$_4$ groups that function to increase the rotational correlation time of the polymers.

Additional R$_3$ groups include those of the following formulas:

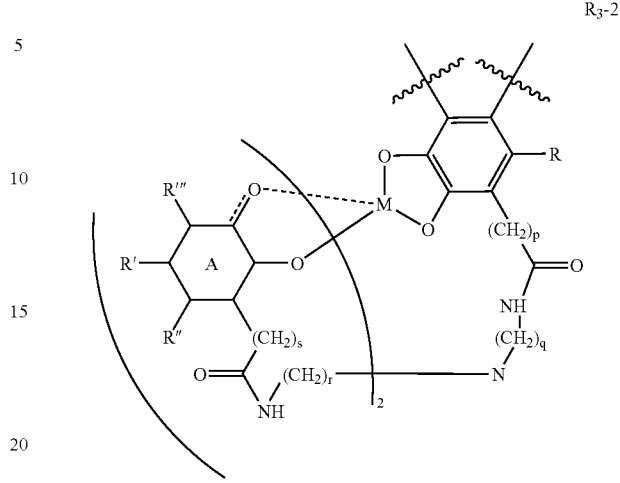

where R, R', R", R''', and M are as defined above and p, q, r, and s are integers ranging from 1 to 3 and one or both of p and s can be 0. M more specifically can be Gd(III), and R, R' and R" more specifically can be alkyl, alkoxy, aryl, aryloxy and amine group which are optionally substituted with one or more halides, hydroxides, alkyl or aryl groups. In specific embodiments r and q are 2 or 3. In specific embodiments s and p are 0 and r and q are 2 or 3. In specific embodiments R', R" or R''' are hydrogen atoms, alkyl groups, particularly alkyl groups having 1-3 carbon atoms, ether groups, esters, amides, hydroxylamines or hydroxylamides. More specifically R', R" and most particularly R''' can be an alkyl (e.g., methyl), alkoxy (e.g., methoxy), ether (e.g., —(CH$_2$)$_k$O—CH$_3$, where k is 1, 2, 3 or 4), hydroxylamine (e.g., —(CH$_2$)$_k$—NH—(CH$_2$)$_l$—OH, where k and l, independently, are 0, 1, 2, or 3, but are not both 0), or hydroxylamide (e.g., —(CH$_2$)$_k$—CO—NH—(CH$_2$)$_l$—OH, where k and l, independently, are 0,1, 2, or 3, but are not both 0). In specific embodiments the A ring is independently selected from A1-A4. In other embodiments one of the A rings is A1-A3. In other embodiments, both A rings are the same. In other embodiments the two A rings are different.

Additional R$_3$ groups include those of the following formula:

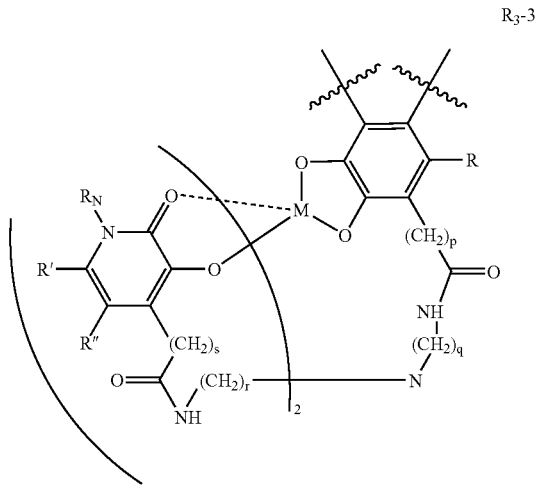

where R, R', R" and M are as defined above and p, q, r, and s are integers ranging from 1 to 3 and one or both of p and s can be 0. M more specifically can be Gd(III), R, R' and R" more specifically can be alkyl, alkoxy, aryl, aryloxy and amine groups which are optionally substituted with one or more halides, hydroxides, alkyl or aryl group and $R_N$ is selected from hydrogen, alkyl, alkenyl, alkynyl, ether, amine, amide, ester or aryl groups wherein one or more carbons of these groups may be substituted with one or more halides, hydroxides, alkyl, alkoxide, aryl or aryloxide groups. In specific embodiments r and q are 2 or 3. In specific embodiments s and p are 0 and r and q are 2 or 3. In specific embodiments R, R' and R" are selected from H, alkyl having 1-3 carbon atoms, alkoxyl having 1-3 carbon atoms, aryloxy (e.g., —CH$_2$—C$_6$H$_5$, or derivatives thereof in which one or more ring H's are replaced with OH, alkyl groups or a halide). In specific embodiments R' and R" are hydrogens, alkyl groups, particularly alkyl groups having 1-3 carbon atoms, ether groups, esters, amides, hydroxylamines or hydroxylamides. More specifically R' and R" can be an alkyl (e.g., methyl), alkoxy (e.g., methoxy), ether (e.g., —(CH$_2$)$_k$O—CH$_3$, where k is 1, 2, 3 or 4), hydroxylamine (e.g., —(CH$_2$)$_k$—NH—(CH$_2$)$_l$—OH, where k and l, independently, are 0, 1, 2, or 3, but are not both 0), or hydroxylamide (e.g., —(CH$_2$)$_k$—CO—NH—(CH$_2$)$_l$—OH, where k and l, independently, are 0, 1, 2, or 3, but are not both 0). In specific embodiments, $R_N$ is an alkyl group, particularly an alkyl having 1-3 carbon atoms and more specifically a methyl group. In other embodiments, $R_N$ is an ether group (e.g., —(CH$_2$)$_k$O—CH$_3$, where k is 1, 2, 3 or 4 or —(CH$_2$)$_k$O—(CH$_2$)$_l$—CH$_3$, where k and l independently are 1-4).

In additional embodiments of all of formulas above, $R_4$ has the formula:

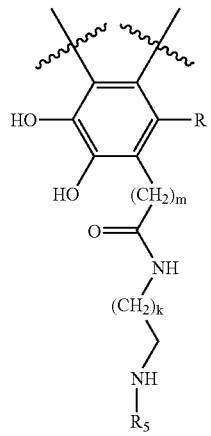

where R is as defined above, k and m are integers ranging independently from 1 to 10 and $R_5$ is an alkyl, alkenyl, alkynyl, aryl, alkoxy, aryloxyl, ketone, positively charged group, negatively charged group, a salt of a positively or negatively charged group. In specific embodiments $R_5$ of a portion of the $R_4$ groups in the metal chelates or chelating agents can be selected from a reactive functional group, a targeting group, a macromolecule, a particle, particularly a nanoparticle, a solid (e.g., the surface of a solid, such as a bead) or a labeling group. In specific embodiments only one or two of the $R_4$ groups of the polymer have $R_5$ that is a reactive functional group, a targeting group, a macromolecule, a particle, particularly a nanoparticle, a solid (e.g., the surface of a solid, such as a bead) or a labeling group.

In independent specific embodiments of all of the above formulas:

M is Gd(III);.

$L_1$ is a linear linker having 3-6 atoms. In other embodiments, $L_2$ are linear linkers having from 3-6 atoms;

All of R, R' and R" are alkyl groups or alkoxide groups, particularly those having 1-3 carbon atoms;

$R_1$ is a phenyl group or a substituted phenyl group (e.g., substituted with one or more halides or hydroxide groups);

$R_2$ is a ketone group;

$R_2$ is a —(CH$_2$)$_k$—CO—(CH$_2$)$_m$—CH$_3$ group where k and m are integers ranging from 1 to 6 and one of k or m can be zero; and $R_S$ is a group -$L_1$-$R_X$, where $R_X$ is a charged group where $L_1$ is a linker group as defined above where in more specific embodiments -$L_1$- is a linear group having 3-10 atoms. In specific embodiments $R_X$ is —NH—C(=NH$_2^+$)—NH$_2$.

The invention further relates to polymeric chelating agents, useful for chelating metals, which have formulas as above wherein there is no transition metal or lanthanide metal complexed in the $R_3$ chelating group. The $R_3$ groups of chelating agents can have the structure:

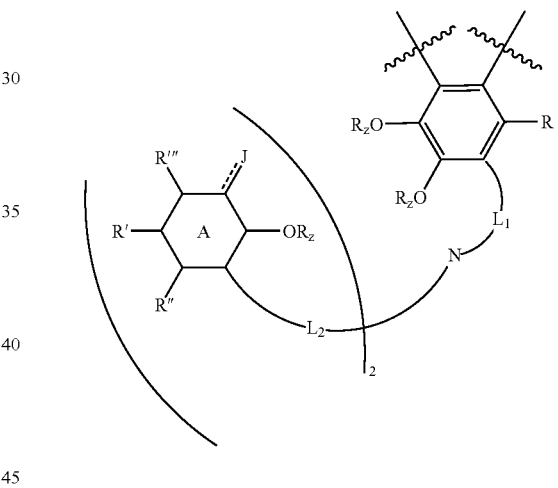

where J is O or OR$_z$, the dashed line from J to the ring indicates the presence of a bond dependent upon selection of J and R$_Z$ is a cation or hydrogen. Useful cations include, among others, singly charged cations (e.g., Na$^+$, Li$^+$, K$^+$, etc), and doubly charged cations (Ca$^{2+}$, Mg$^{2+}$, etc.). In specific embodiments, cations can be any pharmaceutically acceptable cation. In specific embodiments, chelating agents are salts. Dependent upon the nature of the Rs group in the spacer group, it may exist in a neutral or charged form with appropriate counterion. In specific embodiments where Rs comprises a —NHC(=NH)—NH$_2$ group, the group may be in the charged form —NHC(=NH$_2^+$)—NH$_2$Y, where Y is a singly charged anion (e.g., Cl$^-$) and in specific embodiments Y is a pharmaceutically acceptable anion.

The invention further relates to monomeric chelating agents and metal chelates, particularly those of transition metals and lanthanide metals and more specifically those of Gd(III) which are useful as contrast agents in magnetic resonance imaging (MRI) for diagnostic, clinical and biomedical research applications having the formulas:

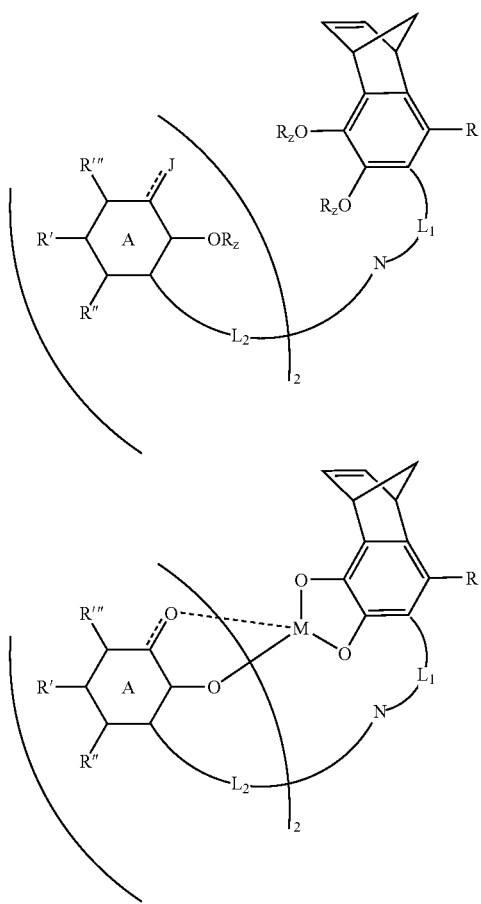

and salts thereof where the variables J, R, R', R", R'", Rz, ring A, $L_1$, $L_2$, and M can take any of the forgoing generic and more specific definitions. In specific embodiments the A rings are both A1.

The invention also provides block polymers which are chelating agents and metal chelates in which the block polymer comprises one or more linear blocks, which are generated by ROMP. In such block polymers, one block comprises one or more hydroxypyridonate (HOPO)-based chelating moieties integrated into the polymer backbone. These chelating moieties can bind metals as noted above. In specific embodiments, the invention provides block polymeric metal chelates of transition metals, actinide metals, and lanthanide metals, and more specifically provides block polymers that chelate one or more Gd(III) metal ions and which are useful as MRI contrast agents. Polymer blocks can also present targeting agents, solubilizing groups, labeling groups, or groups that change the rotational correlation time of the block polymers.

In one embodiment, the block polymers are graft block polymers. A graft polymer is a polymer comprising a graft macromolecule which is a macromolecule with one or more species of polymers connected to a main chain as side chains. The graft side chain blocks are typically different in structure or configuration compared to the main chain polymer. Thus, a graft block polymer comprises a main chain polymer and one or more than one graft side chain polymer. The graft block polymers that are chelating agents and metal chelates have main chains that are ROMP-derived polymer blocks carrying one or more (HOPO)-based chelating moieties integrated into the polymer backbone. The graft side polymer can be any polymer that can be grafted to the main chain ROMP-derived polymer to increase its rotational correlation time. In specific embodiments, the graft side chains are also ROMP-derived polymer blocks. In preferred embodiments, the graft side chain ROMP-derived polymers do not contain metal chelating groups. In specific embodiments, the main chain ROMP-derived polymer contains at least one and preferably more than side chain which is itself a monomer for ROMP. In this embodiment, the graft polymer block side groups can be formed by ROMP from the one or more ROMP monomer side groups of the main chain. The ROMP-derived main chain polymer can contain one or more chelating groups and metal-containing chelating groups $R_3$ as disclosed herein. The ROMP-derived main chain polymer can contain one or more spacer groups as defined herein. The main chain ROMP-derived polymer can have any of the structures as defined herein for polymeric metal chelates and chelating agents, but in addition carries at least one and preferably more than one side chain which is a ROMP monomer to allow formation of the graft polymer side chains.

In specific embodiments, the invention provides graft block polymers that are MRI contrast agents particularly those carrying one or more Gd(III) ions in HOPO-based chelating groups in the main chain. The graft block polymers will exhibit slower molecular tumbling rates compared to linear polymeric metal chelates and as a result will exhibit increased rotational correlation times and exhibit increased relaxivity to provide improved MRI contrast enhancing agents. In specific embodiments, the graft block side chains of the MRI contrast agents are also ROMP-derived polymers and preferably these side chain ROMP-derived polymers carrying a plurality of side chains which are hydrophilic and promote water-solubility of the graft block polymer. Exemplary graft block copolymers of this invention are illustrated in Schemes 2 and 3.

The invention further relates to specific intermediates useful for the synthesis of polymeric chelates herein having the formula:

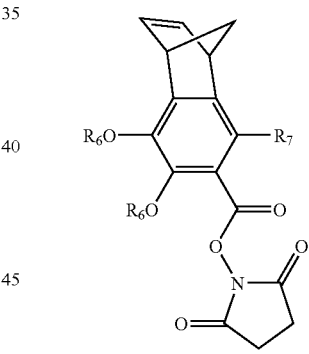

where $R_7$ can take any value of R above, and in specific embodiments is an alkyl or alkoxyl group ($OR_6$) and $R_6$ can be selected from alkyl, alkenyl, alkynyl and aryl wherein one or more carbon atoms can be replaced with O, $NR_N$ (where $R_N$ is as defined above), CO, $CONR_N$, $COOR_N$, and wherein $R_6$ can also be an alcohol protecting group. The invention relates to methods of making metal chelating agents and metal chelates employing this intermediate.

The invention additionally relates to methods of using the metal chelating agents and metal chelates of this invention. More specifically, the invention relates to the use of metal chelates of this invention, particularly those in which M is Gd(III) in magnetic resonance imaging applications. More specifically, the invention provides a method for performing contrast enhanced MRI on an individual comprising the steps of administering to the individual an amount of a monomeric or preferably a polymeric Gd(III) chelate of this invention (one or more of any of the above formulas) that is sufficient to enhance contrast in the MRI and collecting MRI data from the individual. In specific embodiments, the individual is a mammal and in other embodiments the individual is a human.

The invention additionally provides pharmaceutical compositions for administration to individual to be subjected to MR imaging comprising one or more MRI contrast agents, particularly one or more polymeric MRI contrast agent of this invention. These compositions comprise an amount of the agent effective for enhancing an MR image and a pharmaceutically acceptable carrier.

DETAILED DESCRIPTION OF THE INVENTION

Figure 1:
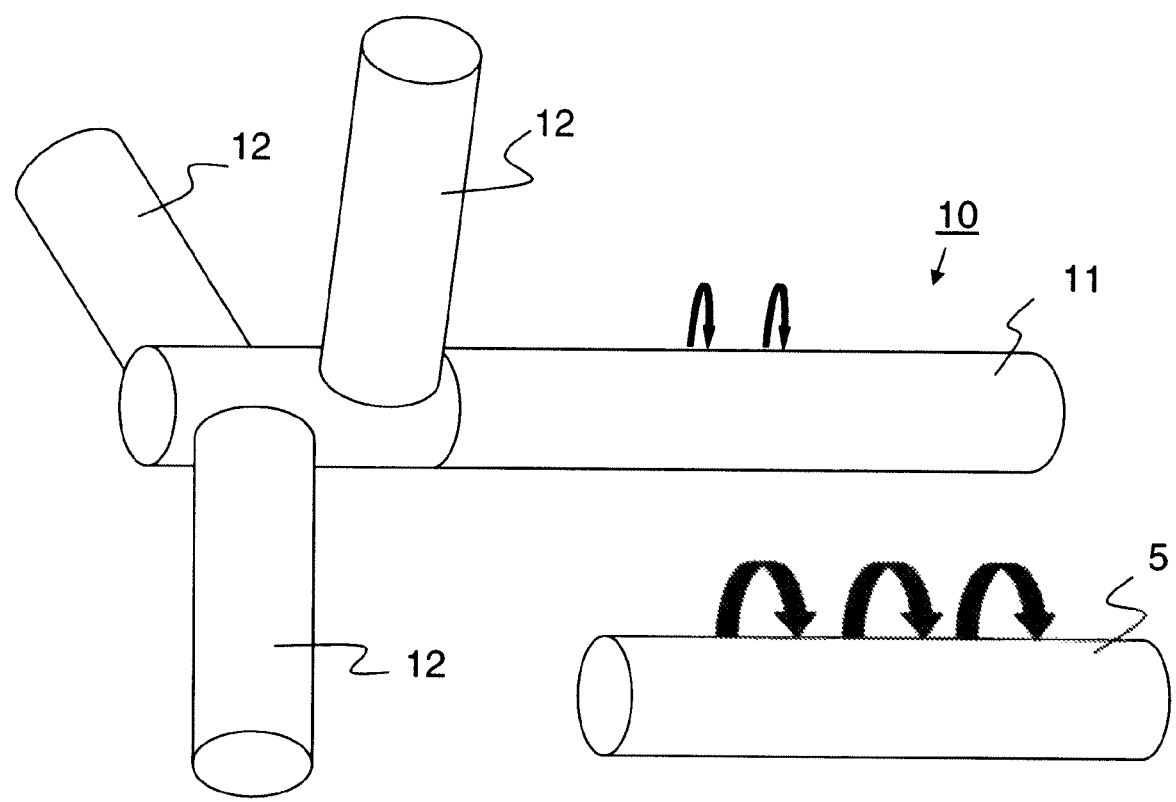
FIG. 1 is a schematic illustration comparing a linear polymer (5) with a graft block polymer (10). The graft polymer contains a main chain (11) and several graft block side chains (12).

This invention relates in large part to polymeric metal chelates and polymeric chelating agents formed using ROMP. Polymeric chelating agents are useful for binding to (i.e., chelating) one or more metal ions and thus forming metal chelates. Polymeric chelating agents of this invention are useful generally in any application in which art-known chelating agents are currently employed, such as in purification methods and in analytical methods. Polymeric metal chelates have a variety of uses including, among others, applications in therapy, diagnostics, clinical research, biological research, and in analytical methods. Metals that can be chelated by the chelating agents of this invention to form metal chelates generally include transition metals, actinide metals and lanthanide metals, and more specifically to Gd(III) and Dy, Fe, Mn, Pu, U, Eu, Cu and Zn (in various oxidation states). Polymeric metal chelates of Gd(III) are particularly useful as MRI contrast enhancing agents. The invention further relates to certain new monomeric chelating agents and metal chelates, including metal chelates of Gd(III) useful as MRI contrast agents.

The polymeric chelating agents and metal chelates of this invention incorporate chelating groups into the backbone of a ROMP-derived polymer. The structures of various ROMP-derived polymer backbones are illustrated in formulas 1, 2, 2A, 2B, 3, 3A and 3B. Integration of the chelating group into the polymer backbone means that functional groups directly bonded to the polymer backbone are part of the chelating group. The chelating group is not usually tethered to the polymer backbone via a linker. Scheme 1 illustrates several examples showing how the chelating group (without chelated metal ion) are integrated into different ROMP-derived backbones. Variables in Scheme 1 are as defined above. Each individual polymeric chelating agent and metal chelate described and/or shown herein is intended to be incorporated to the extent that it can be specifically included or excluded in a claim, if necessary.

The polymeric and monomeric metal chelates and MRI contrast agents of this invention are generally water-soluble. MRI contrast agents which exhibit significant water solubility provide benefit because the agents are typically administered in multigram dosages to the individual subject to the MRI assay and more water soluble agents require generally lower administration volumes which provide for ease of administration. The MRI contrast agents of this invention generally exhibit water-solubility that is significantly greater than that of currently-employed clinical MRI contrast agents.

Relaxivity is a measure of the ability of an agent to enhance contrast in a magnetic resonance image. Relaxivities were determined as the slope of the line generated by plotting the inverse of $T_1$ relaxation time versus concentration. Relaxivity is measured in units of $mM^{-1}$ $s^{-1}$. For polymers which carry more than one metal ion (i.e., Gd(III)), it is useful to examine relaxivity/metal ion (i.e., per Gd(III) ion). Monomer contrast agents of this invention (as exemplified by compound 11, see the Examples) exhibit relaxivity of the order of 10 $mM^{-1}$ $s^{-1}$. The relaxivities of exemplary shorter (e.g., DP=8) and longer polymeric contrast agents of this invention can be compared. For example, a shorter polymeric contrast agent (agent 10a, see the Examples), which on average contains 2 Gd(III)/polymer, exhibits relaxivity of the order of 20 $mM^{-1}$ $s^{-1}$—relaxivity that is approximately additive with Gd(III) ion. In contrast, a significant increase in per Gd(III) ion relaxivity (i.e. better than additive) is observed for longer polymeric contrast agents as exemplified by agent 10b (see the Examples), which has DP of 30 and on average carries 7.5 Gd(III) ions. Thus, longer polymeric contrast agents of this invention are generally preferred as long as they remain water-soluble.

In specific embodiments, linear polymeric chelating agents herein can have DP ranging from 8-100, DP ranging from 10 to 50, DP ranging from 20 to 40, DP ranging from 25 to 35 and DP of 30. DP is the degree of polymerization and is the number of monomer units in the polymer.

The invention also relates to block polymers comprising one or more blocks that are ROMP-derived polymers that in turn contain one or more hydroxypyridonate (HOPO)-based chelating moieties integrated into the polymer backbone. These chelating moieties can bind metals as noted above. In specific embodiments, the invention provides block polymeric metal chelates of transition metals, actinide metals, or lanthanide metals, and more specifically provides block polymers that chelate one or more Gd (III) metal ions and which are useful as MRI contrast agents.

More specifically the invention relates to graft block polymers which are chelating agents and metal chelates. A graft polymer is a polymer comprising a main chain polymer block and one or preferably more than one graft side chain blocks. The side chain blocks are typically different in structure (e.g., polymer backbone, side-chain composition, length, etc.) and/or configuration compared to the main chain polymer block.

Specific graft block polymers that are chelating agents and metal chelates have main chains that are ROMP-derived polymer blocks carrying one or more HOPO-based chelating moieties integrated into the polymer backbone. The graft polymer portion can be any polymer that can be grafted to the main chain ROMP-derived polymer. In specific embodiments, the graft side chains are also ROMP-derived polymer blocks which preferably differ from the main chain block. In preferred embodiments, the graft side chain ROMP-derived polymers do not contain metal chelating groups.

In specific embodiments, the main chain ROMP-derived polymer contains at least one and preferably more than one side chain which is itself a monomer for ROMP. In this embodiment, the graft polymer block side groups can be formed by ROMP from the one or more ROMP monomer side groups of the main chain. The ROMP-derived main chain polymer can contain one or more chelating groups and metal-containing chelating groups $R_3$ as disclosed herein. The ROMP-derived main chain polymer can contain one or more $R_4$ groups as defined herein. In specific embodiments, the main chain generated by ROMP can contain $R_4$ groups that are spacer groups, solubilizing groups, targeting groups, labeling groups or groups that increase the rotational correlation time of the polymer. The main chain polymer generated by ROMP can have any of the structures as defined herein for ROMP-derived polymeric metal chelates and chelating agents, but, in addition, carries at least one and preferably more than one side chain which is a ROMP monomer to allow formation of the graft polymer side chains. In specific embodiments, the main chain block carries chelating side groups and one or more than one grafted side chain ROMP-derived polymer blocks. In specific embodiments, the graft block polymers herein carry one or more chelating groups (with or without chelated metal), one or more solubilizing groups, one or more targeting groups, and/or one or more labeling groups. The graft block polymers may also contain one or more $R_4$ groups which serve to increase the rotational correlation time of the polymer.

The graft side chain ROMP-derived polymer can have any of the ROMP-derived backbone structures as described herein and can carry any of the spacer side groups as described herein. In specific embodiments, the graft side chain ROMP polymer carries side groups which are hydrophilic and which promote water-solubility of the block polymer. Preferably the ROMP-derived main chain ranges in DP from about 10-40 and more preferably ranges in DP from about 10-20. Preferably, the graft side chain ROMP-derived polymers range in DP from about 5 to about 50 and more preferably range in DP form 10 to 30. In specific embodiments, the main chain block has DP of 10-15 and the side chain block have DP of 15 to 30. In specific embodiments there are 2-4 side chain blocks. In specific embodiments, the main chain block comprises on average 10 monomers carrying chelating groups ($R_3$) and on average 4 monomers to which side chain grafts are formed.

FIG. 1 is a schematic illustration comparing a linear polymer 5 with a graft block polymer 10 which contains a main chain 11 and several graft block side chains 12. The arrows indicate that the graft block polymer will tumble more slowly around the indicated axis than the linear polymer. This indicates the graft block polymer will exhibit an increased rotational correlation time compared to the linear polymer. Polymers carrying chelated Gd(III) ions which have higher rotational correlation times will exhibit enhanced potency as MRI contrast agents.

Schemes 2 and 3 illustrate exemplary graft block polymers in which the main chain ROMP-derived block polymer carries chelating groups. Scheme 2 illustrates grafting of ROMP-derived polymer side chains onto a ROM-derived main chain. In this scheme, a precursor main chain ROMP-derived polymer is reacted to graft a plurality of graft side chain ROMP-derived polymers to the main chain. The precursor ROMP-derived polymer main chain carries x side groups carrying reactive groups that can subsequently be functionalized to HOPO-based chelating groups and carries y side groups that are ROMP monomers for forming grafts. The graft side chains are formed by reacting a ROMP monomer carrying a protected side group, which, when deprotected, will be a hydrophilic, charged group that promotes water-solubility of the polymer. In the illustrated scheme, z is the average number of monomer units in the graft side chain ROMP-derived polymer. In specific embodiments, x+y ranges from 10-20 and z ranges from 5 to 30. In specific embodiments, the ratio of x/y ranges from 0.5 to 5 and in specific embodiments, x/y is 2-3. In specific embodiments, z is 18-25 and in other embodiments z is 20.

Scheme 3 illustrates the synthesis of a ROMP-derived polymer that is used as the main chain polymer in the graft block polymer. It will be appreciated that the ROMP-derived main chain block can be prepared having any of the polymer backbone structures illustrated herein and having any of the $R_1$ or $R_2$ groups or having any of the $R_3$ and/or $R_4$ groups as illustrated herein. It will be further appreciated that that the graft side chain ROMP-derived polymers can be prepared having any of the polymer backbone structures illustrated herein and to carry any side chain groups that are illustrated herein. It will be appreciated that the graft block polymer can be derivatized as illustrated in Scheme 1 in view of examples provided herein with any of the HOPO-based chelating groups illustrated herein.

In specific embodiments, polymeric MRI contrast agents of this invention carry on average 3 or more Gd(III) ions. In other embodiments, they carry on average 5 or more Gd(III) ions. In yet other embodiments, they carry on average 7 or more Gd(III) ions. In additional embodiments, they carry on average 10 or more Gd(III) ions.

In specific embodiments, polymeric MRI contrast agents of this invention exhibit relaxivity of about 10 $mM^{-1}$ $s^{-1}$ per Gd(III) ion. In specific embodiments, polymeric MRI contrast agents of this invention exhibit relaxivity of greater than 10 $mM^{-1}$ $s^{-1}$ per Gd(III) ion. In specific embodiments, polymeric MRI contrast agents of this invention exhibit relaxivity of greater than 12 $mM^{-1}$ $s^{-1}$ per Gd(III) ion. In specific embodiments, polymeric MRI contrast agents of this invention exhibit relaxivity of greater than 14 $mM^{-1}$ $s^{-1}$ per Gd(III) ion.

In specific embodiments, metal chelating polymeric compounds of the invention have one or more R3 groups. In specific embodiments, polymers having multiple chelating groups and one or more cell targeting or cytotoxic compounds are presented. Specific embodiments of the invention are trimers or tetramers of only R3 are used as contrast agents for MRI with improved signal over conventionally used chelate contrast agents.

The ratio of chelating side group to spacer group is varied by adjusting the stoichiometry of conjugation of those groups with the polymer backbone. In the specific examples, 0.25 equivalents per monomer of the chelating side group are employed with 0.75 equivalents of the spacer group to give a ratio of spacer to chelating groups of 3:1. The stoichiometry can be varied, as is known in the art, to obtain desired relative amounts of different polymer side chains. It is preferred for MRI contrast agents to have a polymer that has the highest number of chelating groups per polymer that bind Gd(III), while minimizing interference between the chelating groups and preserving polymer solubility in water. Exemplary polymers, in which all of the monomers carry chelating side groups and no spacers, exhibited very low relaxivity values, The observed low relaxivity is believed to be the result of chelating groups blocking water access to adjacent metal chelates.

Chelating agents of this invention can form high stability complexes with Gd(III) compatible with safe administration to individuals subjected to imaging assays.

The term "reactive functional group" is used broadly herein to refer to a functional group which can react to form a bond to a chemical compound of interest, to a particle or the surface of a solid. Reactive functional groups are used herein to form a bond between a metal chelating agent of this invention, e.g., an MRI contrast agent of this invention with a chemical compound of interest or a particle or solid surface such that the agent is attached or bonded to the chemical compound, particle or solid. The bond that is formed is typically a covalent bond, but need not be a covalent bond. A variety of reactive functional groups are known in the art that can be employed for this function. The reactive functional group is chosen based on the structure and chemical reactivity of the agent and the species (compound, particle or surface) to which it is intended to form a bond. Compounds of interest include targeting groups (see below), macromolecules (polysaccharides, proteins, peptides, nucleic acids, and small molecules). Particles and solids of interest include nanoparticles, beads and substrates made of resin, glass, plastics and similar materials, and labeling groups (see below). In specific examples, reactive groups are activated ester groups, which is a generic term used in the art to refer to ester groups that are activated to be more reactive, for example, by the presence of a good leaving group. In specific embodiments N-hydroxysuccinimide esters can be employed as reactive groups.

The linking group that is formed between a chelating agent of this invention and a compound of interest, a particle or a solid can be selectively cleavable. The linking group can be selected such that it can be selectively cleaved by exposure to a reactive species or medium. For example, the bond can be cleavable by a change in pH, exposure to a reactive chemical or biological species (i.e., a reagent or enzyme) or exposure to light of a selected wavelength.

The term "targeting group" is used herein to refer to a chemical moiety that can be attached to a chelating or contrast agent of this invention and which exhibits an affinity for binding to, adsorption on, being absorbed by, or entering into a macromolecule (particularly a biologically functional macromolecule), or a target cell or tissue, such as a cancerous cell or tumor tissue, or a biological fluid, such as blood. A targeting group can be a small molecule, such as a peptide, nucleic acid, receptor ligand, sugar, antigen, or other small molecule exhibiting a binding affinity for a cell surface, receptor or for a macromolecule. A targeting group can be a peptide. The targeting group can also be a macromolecule, including without limit saccharides, polysaccharides, lectins, receptors, ligands for receptors, proteins, antibodies, poly(ethers), dendrimers, poly(amino acids) and nucleic acids. In specific embodiments, the targeting group can bind a component of blood, particularly a protein component of blood, such as serum albumin. A contrast agent comprising a targeting group that binds a blood component can enhance its blood pool residence time and rotational correlation time.

In specific embodiments, targeting groups are linear and cyclic peptides, which may be naturally-occurring or synthetic peptides, such as peptides containing the arginine-glycine-aspartate (RGD) sequence motif. Specific examples of RGD peptides include among others the cyclic peptide RGDFK (Targeting Agent 1) and GGGGGRGDY (Targeting Agent 2). As illustrated below, exemplary peptide targeting agents useful in this invention will contain a peptide sequence for targeting, such as the RGD sequence for targeting to integrins, as well as a functional group, such as an amine, that can be conjugated to the polymer backbone via a reactive group which reacts with amines. The targeting group, may itself contain a spacer group (e.g., for a peptide targeting group a glycine linker) and may further contain a label that facilitates detection of the presence of the targeting group, such as a group that aids in $^1$H-NMR characterization.

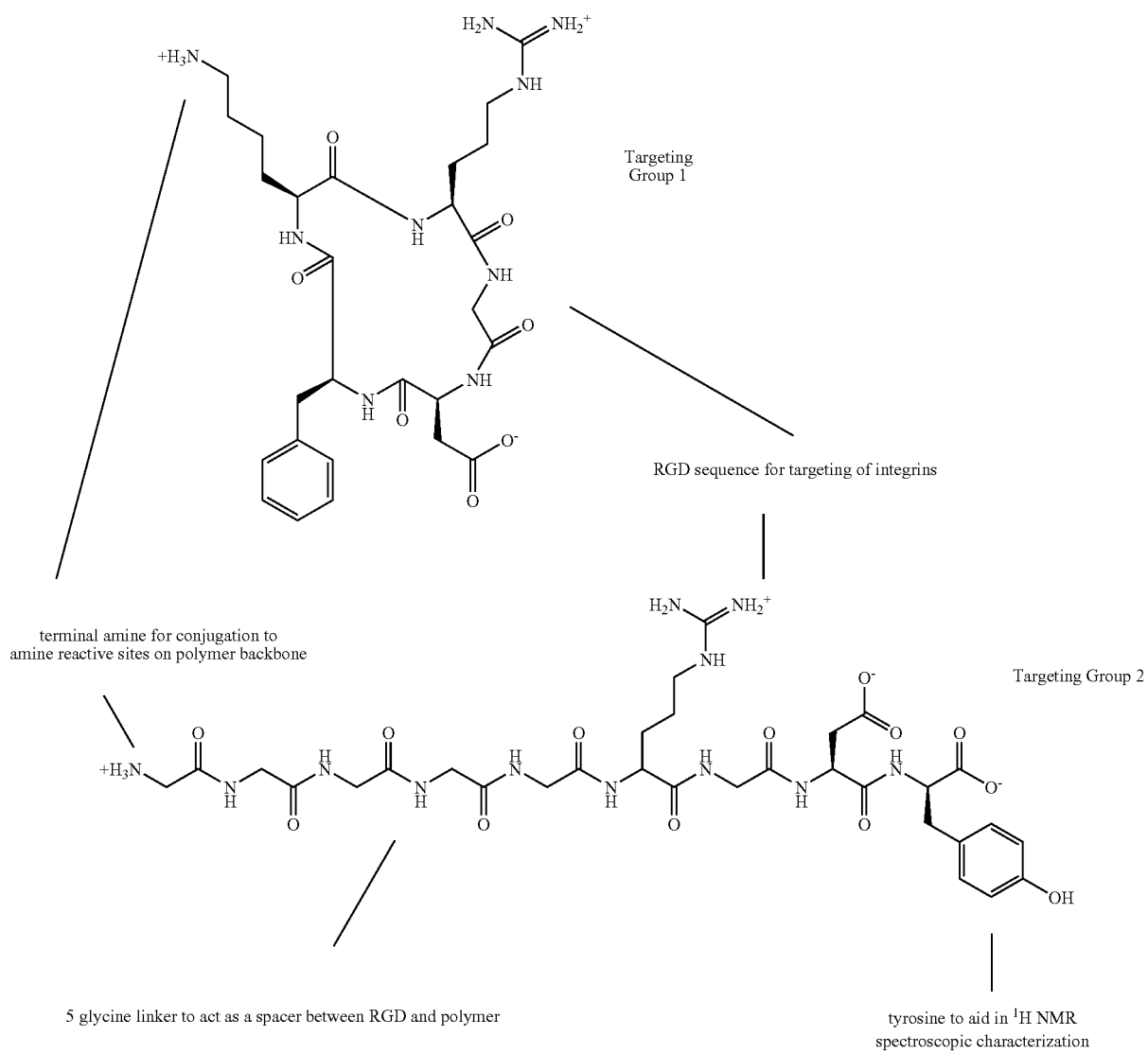

Any targeting group that contains a hydrazine or acylhydrazide (or is derivatized to contain a hydrazine or acylhydrazide), can be readily reacted with the ketone of $R_2$ to link the targeting groups to the metal chelate or chelating agent through the formation of a hydrazone or hydrazide linkage, respectively. Additionally, amine derivates of targeting groups can be attached at $R_2$, $R_s$ or $R_5$ as defined in the summary of the invention above, through an amide linker. Various derivatives of targeting peptides can be attached to the polymers herein through various linkers, including among others, urea, thiourea, and squarate. In specific embodiments, amine-containing targeting groups (and guanidinium-substituted amines) can be reacted with the N-hydroxysuccinimide esters to connect them to the backbone. It will be appreciated in the art that a variety of linkers can be employed to couple or conjugate derivatized targeting groups to the polymers of this invention.

The term "labeling group" is used herein to refer to any chemical species, particle or solid which exhibits or can be stimulated to exhibit a detectable signal. The label may be a radioactive label, a fluorescent label, a small molecule label (e.g., biotin), a reactive label (e.g., a species whose reaction with a reagent or substrate can be detected, for example an enzyme). In specific embodiments, the labeling group is a fluorophore. Exemplary fluorophores are those that contain a hydrazine group which can be readily reacted with the chelating and MRI contract agents of this invention. In specific embodiments, the labeling group is a radioactive label.

Any labeling groups, particularly a fluorophore, that contains a hydrazine or acylhydrazide can be readily reacted with the ketone at $R_2$ to link the labeling group (e.g., fluorophore) to the metal chelator or chelating agents through the formation of a hydrazone or hydrazide linkage, respectively. Additionally, amine derivatives of labeling groups can be attached at $R_2$, $R_s$ or $R_5$ as defined in the summary of the invention above, through an amide linker. Other linkers can be employed as well with derivatized labeling groups including among others, urea, thiourea, and squarate. In specific embodiments, amine-containing labeling groups (and guanidinium-substituted amines) can be reacted with the N-hydroxysuccinimide esters to connect them to the backbone. It will be appreciated in the art that a variety of linkers can be employed to couple or conjugate a labeling group to the polymers of this invention.

In a specific embodiment, the attachment of one or more fluorescent labels to a MRI contrast agent of this invention would enable both fluorescent microscopy and MR imaging—which can be useful, for example, in biological research applications, in developmental biology, or verification of MR images with histology. The attachment of one or more radioactive labels to a MRI contrast agent of this invention would be useful for dual imaging with PET (positron emission tomography) or SPECT (single photon emission computed tomography). Radioactive labels for PET include carbon-11, oxygen-15, fluorine-18, and bromine-75; while radioactive labels for SPECT include chelates of Xenon-133, Technetium-99, or Iodine-123. The radiolabels can, for example, be conjugated at $R_2$ through a hydrazone or acylhydrazide linker, similar to that mentioned for above. Additionally, amine derivates of either fluorescent or radiolabels could be attached at $R_2$, $R_s$ or $R_5$ through an amide linker.

In specific embodiments, the chelating agents, metal chelates, and MRI contrast agents of this invention can be bonded or attached to particles or solid surfaces. The attachment to particles, solids or surfaces can be formed through a selectively cleavable linker such that the agent can be selectively separated from the particle, solid or surface. In specific embodiments, the particles are nanoparticles (See, for example, the description in Brigger et al. Nanoparticles in cancer therapy and diagnosis, Advanced Drug Delivery Reviews 54 (2002) 631-651) which are useful in cancer therapy and diagnosis. The MRI contrast agents of this invention can be attached to nanoparticles loaded with anticancer drugs/targeted to cancer cells to provide combination diagnostic/therapeutic agents.

Chemical reactions similar to those discussed above for attachment of labeling groups and targeting groups can be employed to link chelating agents and metal chelates of this invention to particles, such as nanoparticles, and to solids.

The polymeric and monomeric chelating agents and metal chelates of this invention can be prepared by methods described herein in the Examples and or by routine adaptation of these methods by varying the type and relative amounts of starting monomers, by varying reagents and other reactants as is known in the art and by employing additional methods that are known in the art. In exemplary embodiments, polymers of this invention can be prepared as illustrated in the specific examples herein in which a precursor ROMP-derived polymer comprising monomers carrying reactive groups (e.g., activated esters) is reacted with a mixture of components that are to be attached to the polymer. Scheme 2 illustrates, for example, synthesis of polymeric metal chelates in which a portion of the monomers of the polymer carry chelating groups and a portion carry spacer/solubilizing groups. The various polymeric chelating agents and metal chelates of this invention can be prepared by methods analogous to those illustrated in the examples.

The methods illustrated in the examples and Scheme 3 can also be employed to prepare main chain ROMP-derived polymers of the graft block polymers of this invention. Graft block polymers of this invention can be synthesized for example employing methods as illustrated in Scheme 2.

In general the terms and phrases used herein have their broadest art-recognized meaning, which can be found by reference to standard texts, journal references and contexts known to those skilled in the art. Any definitions provided are provided to clarify the specific use of these terms and phrases in the context of the invention.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 30 carbon atoms and more preferred are those that contain 1-22 carbon atoms. Short alkyl groups are those having 1 to 6 carbon atoms including methyl, ethyl, propyl, butyl, pentyl and hexyl groups, including all isomers thereof. Long alkyl groups are those having 8-30 carbon atoms and preferably those having 12-22 carbon atoms as well as those having 12-20 and those having 16-18 carbon atoms. The term "cycloalkyl" refers to cyclic alkyl groups having preferably 3 to 30 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantanyl, and the like.

The term "alkenyl" refers to a monoradical of a branched or unbranched unsaturated hydrocarbon group and to cycloalkenyl groups having one or more rings wherein at least one ring contains a double bond. Unless otherwise indicated preferred alkyl groups have 1 to 30 carbon atoms and more preferred are those that contain 1-22 carbon atoms. Alkenyl groups may contain one or more double bonds (C=C) which may be conjugated or unconjugated. Preferred alkenyl groups are those having 1 or 2 double bonds and include omega-alkenyl groups. Short alkenyl groups are those having 2 to 6 carbon atoms including ethylene (vinyl), propylene, butylene, pentylene and hexylene groups, including all isomers thereof. Long alkenyl groups are those having 8-30 carbon atoms and preferably those having 12-22 carbon atoms as well as those having 12-20 carbon atoms and those having 16-18 carbon atoms. The term "cycloalkenyl" refers to cyclic alkenyl groups of from 3 to 30 carbon atoms having a single cyclic ring or multiple condensed rings in which at least one ring contains a double bond (C=C). Cycloalkenyl groups include, by way of example, single ring structures such as cyclopropenyl, cyclobutenyl, cyclopentenyl, cyclooctenyl, cylcooctadienyl and cyclooctatrienyl.

The term "alkynyl" refers to a monoradical of an unsaturated hydrocarbon having one or more triple bonds (C≡C). Unless otherwise indicated preferred alkyl groups have 1 to 30 carbon atoms and more preferred are those that contain 1-22 carbon atoms. Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms.

Alkyl, alkenyl, alkynyl and aryl groups may be substituted or unsubstituted. Alkyl, alkenyl, alkynyl and aryl groups may be optionally substituted as described herein and may contain non-hydrogen substituents dependent upon the number of carbon atoms in the group and the degree of unsaturation of the group. Unless otherwise indicated substituted alkyl, alkenyl, alkynyl and aryl groups preferably contain 1-10, and more preferably 1-6, and more preferably 1, 2 or 3 non-hydrogen substituents. Preferred non-hydrogen substituents unless otherwise stated are halides, hydroxides, alkyl, and aryl groups (e.g., benzyl or phenyl groups).

The term alkoxy (or alkoxide) refers to a —O-alkyl group, where alkyl groups are as defined above. The term alkeneoxy (alkenoxide) refers to a —O-alkenyl group where alkenyl groups are as defined above and wherein a double bond is preferably not positioned at the carbon bonded to the oxygen. The term alkyneoxy (alkynoxide) refers to a —O-alkynyl group where alkynyl groups are as defined above and wherein a triple bond is not positioned at the carbon bonded to the oxygen.

The term "aryl" refers to a group containing an unsaturated aromatic carbocyclic group of from 6 to 22 carbon atoms having a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Aryls include phenyl, naphthyl and the like. Aryl groups may contain portions that are alkyl, alkenyl or alkynyl in addition to the unsaturated aromatic ring(s). The term "alkaryl" refers to the aryl groups containing alkyl portions, i.e., -alkylene-aryl and -substituted alkylene-aryl). Such alkaryl groups are exemplified by benzyl, phenethyl and the like.

The term "aryloxide" or "aryloxy" refers to an —O-aryl group.

The term "thioalkoxyl" refers to an alkyl group attached to the remainder of the molecule via a sulfur atom (—S-alkyl).

The term "thioether" refers to an ether group attached to the remainder of the molecule via a sulfur atom.

The term "ester" refers to chemical entities containing a —COO— moiety, as understood in the art, and in particular can include groups of the form RCO—O— or —CO—OR where R is optionally substituted alkyl, alkenyl, alkynyl or aryl. The term "activated ester" is understood in the art to refer to an ester group activated for reaction, for example, by the presence of a good leaving group.

The term "ether group" also "alkoxyalkyl" refers to an alkyl group in which one or more —CH$_2$— groups are replaced with —O—. Unless otherwise specified preferred alkoxyalkyl groups have from 3 to 30 carbon atoms and more preferably have 6 to 22 carbon atoms. Ether groups include groups of the formula: —[(CH$_2$)$_a$—O—]$_b$—CH$_3$ where a is 1-10 and b is 1-6. More specifically, a can be 2, 3 or 4 and b can be 1, 2 or 3. Alkoxyalkyl groups can be branched by substitution of one or more carbons of the group with alkyl groups. The term "thioether" refers to refers to an alkyl group in which one or more —CH$_2$— groups are replaced with —S—. Unless otherwise specified preferred thioether groups have from 3 to 30 carbon atoms and more preferably have 6 to 22 carbon atoms. Thioether groups include groups of the formula: —[(CH$_2$)$_a$—S—]$_b$—CH$_3$ where a is 1-10 and b is 1-6. More specifically, a can be 2, 3 or 4 and b can be 1, 2 or 3. Thioether groups can be branched by substitution of one or more carbons of the group with alkyl groups.

The term "alkylene" refers to a diradical of a branched or unbranched saturated hydrocarbon chain, which unless otherwise indicated can have 1 to 10 carbon atoms, or 1-6 carbon atoms, or 2-4 carbon atoms. This term is exemplified by groups such as methylene (—CH$_2$—), ethylene (—CH$_2$CH$_2$—), more generally —(CH$_2$)$_n$—, where n is 1-10 or more preferably 1-6 or n is 2, 3 or 4. Alkylene groups may be branched, e.g., by substitution with alkyl group substituents. Alkylene groups may be optionally substituted as described herein. Alkylene groups may have up to two non-hydrogen substituents per carbon atoms. Preferred substituted alkylene groups have 1, 2, 3 or 4 non-hydrogen substituents. Hydroxy-substituted alkylene groups are those substituted with one or more OH groups.

The term "alkoxyalkylene" refers to a diradical of a branched or unbranched saturated hydrocarbon chain in which one or more —CH$_2$— groups are replaced with —O—, which unless otherwise indicated can have 1 to 10 carbon atoms, or 1-6 carbon atoms, or 2-4 carbon atoms. This term is exemplified by groups such as —CH$_2$OCH$_2$—, —CH$_2$CH$_2$OCH$_2$CH$_2$—, —CH$_2$CH$_2$OCH$_2$CH$_2$OCH$_2$CH$_2$— and more generally —[(CR"$_2$)$_a$—O—]$_b$—(CR"$_2$)$_c$, where R" is hydrogen or alkyl, a is 1-10, b is 1-6 and c is 1-10 or more preferably a and c are 1-4 and b is 1-3. Alkoxyalkylene groups may be branched, e.g., by substitution with alkyl group substituents.

The term "amino" or "amine group" refers to the group —NH$_2$ or to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen. Specific amine groups are those in which each R can be hydrogen or an optionally substituted alkyl group, including hydroxide-substituted amines.

The term "amide" refers to a group containing the —CO—NR— moiety where R is selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic. Specific amide groups are optionally substituted alkyl amides, including hydroxide-substituted amides.

The term "heterocycle" or "heterocyclic" refers to a monoradical saturated or unsaturated group having a single ring or multiple condensed rings, from 2-22 carbon atoms and from 1 to 6 hetero atoms, preferably 1 to 4 heteroatoms, selected from nitrogen, sulfur, phosphorus, and/or oxygen within at least one ring. Heterocyclic groups may be substituted.

Haloalkyl refers to alkyl as defined herein substituted by one or more halides (e.g., F—, Cl—, I—, Br—) as defined herein, which may be the same or different. A haloalkyl group may, for example, contain 1-10 halide substituents. Representative haloalkyl groups include, by way of example, trifluoromethyl, 3-fluorododecyl, 12,12,12-trifluorododecyl, 2-bromooctyl, 3-bromo-6-chloroheptyl, and the like. Haloalkyl groups include fluoroalkyl groups.

In the definitions herein optional substitution includes substitution with one or more halogens, nitro groups; cyano groups; isocyano groups; thiocyano groups (—S—C≡N); isothiocyano groups (—N=C=S); azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups; thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; various silyl groups, including alkyl-substituted silyl groups. Some particular ring substituents include: —Br, —OH, —$SO_3$, isothiocyano, thiocyano, carboxylic acid and carboxylic acid derivatives, —$NH_2$, amines and —$NO_2$ and any salts thereof.

Compounds of the present invention, and salts or esters thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, the compounds may have trans and cis isomers and may contain one or more chiral centers, therefore existing in enantiomeric and diastereomeric forms. The invention can encompass all such isomers, individual enantiomers, as well as mixtures of cis and trans isomers, mixtures of diastereomers; non-racemic and racemic mixtures of enantiomers (optical isomers); and the foregoing mixtures enriched for one or more forms; except as stated otherwise herein. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure.

Specific names of compounds are intended to be exemplary, as it is known that one of ordinary skill in the art can name the same compounds differently. When a compound is described herein such that a particular isomer, enantiomer or diastereomer of the compound is not specified, for example, in a formula or in a chemical name, that description is intended to include each isomers and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of"

does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning additional assay methods, sources of starting materials and biological materials, additional starting materials, additional reagents, additional methods of synthesis, additional methods of analysis, additional biological materials and additional uses of the invention.

SCHEME 1

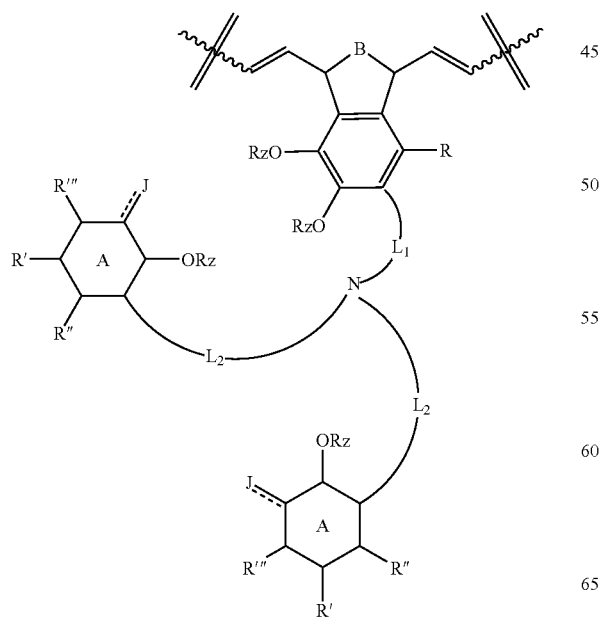

-continued

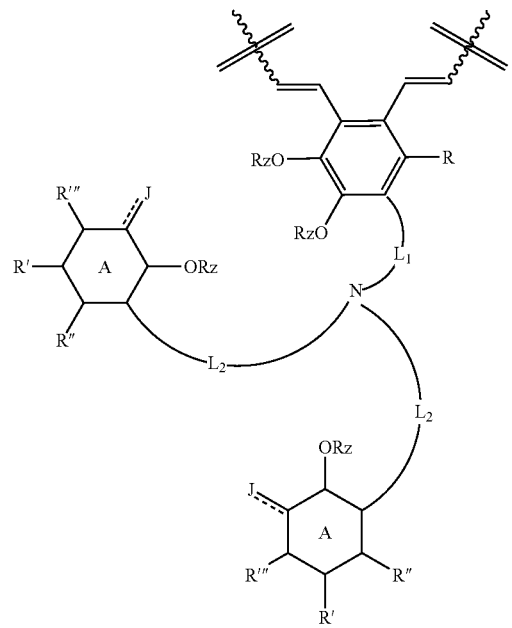

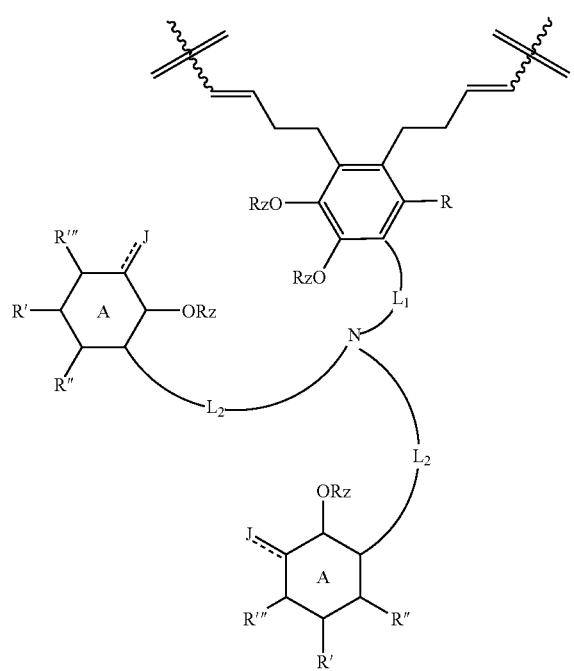

SCHEME 2
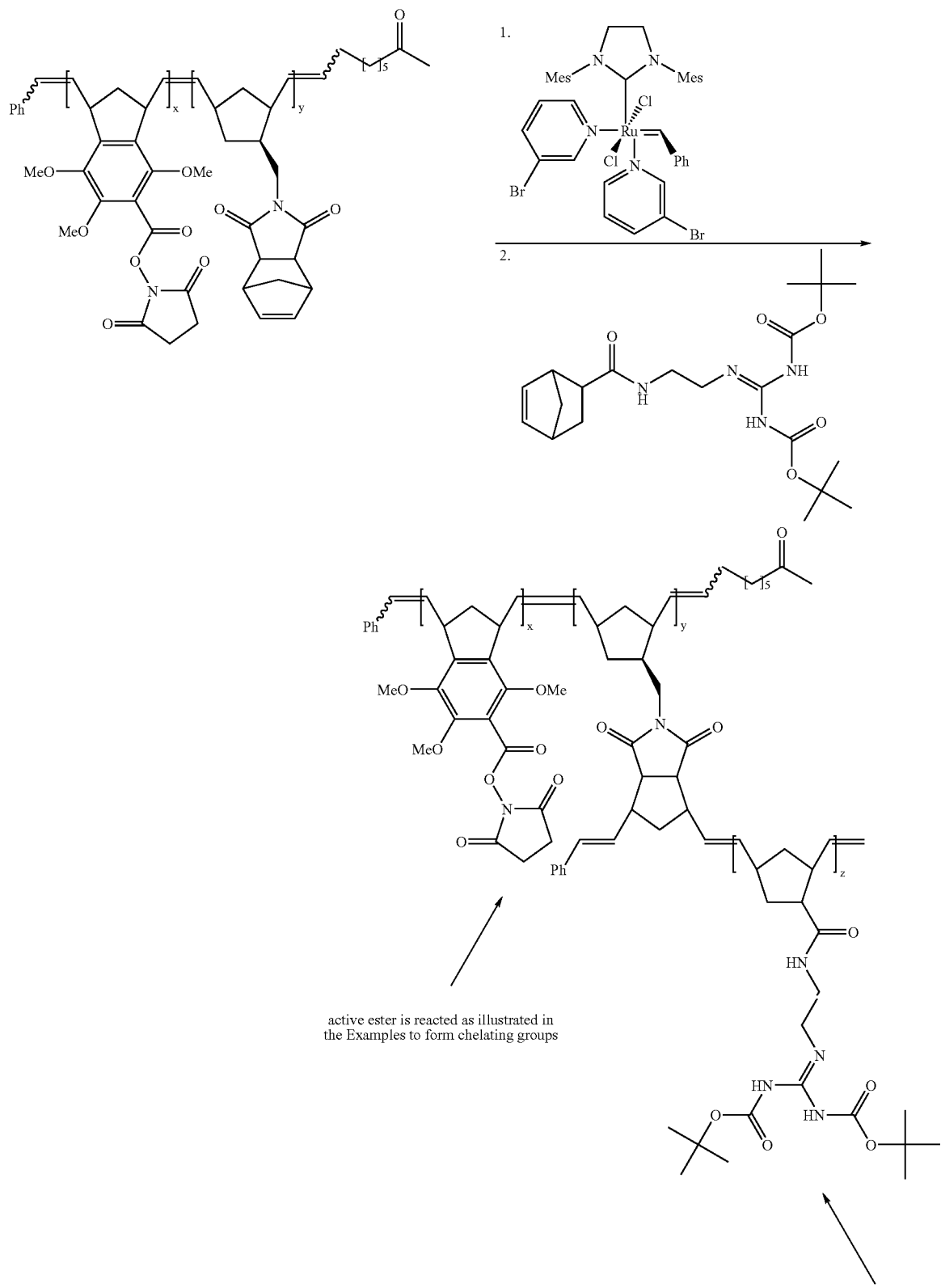
active ester is reacted as illustrated in
the Examples to form chelating groups
after Boc removal with trifluoroacetic
acid, charged groups will maintain
aqueous solubility

SCHEME 3

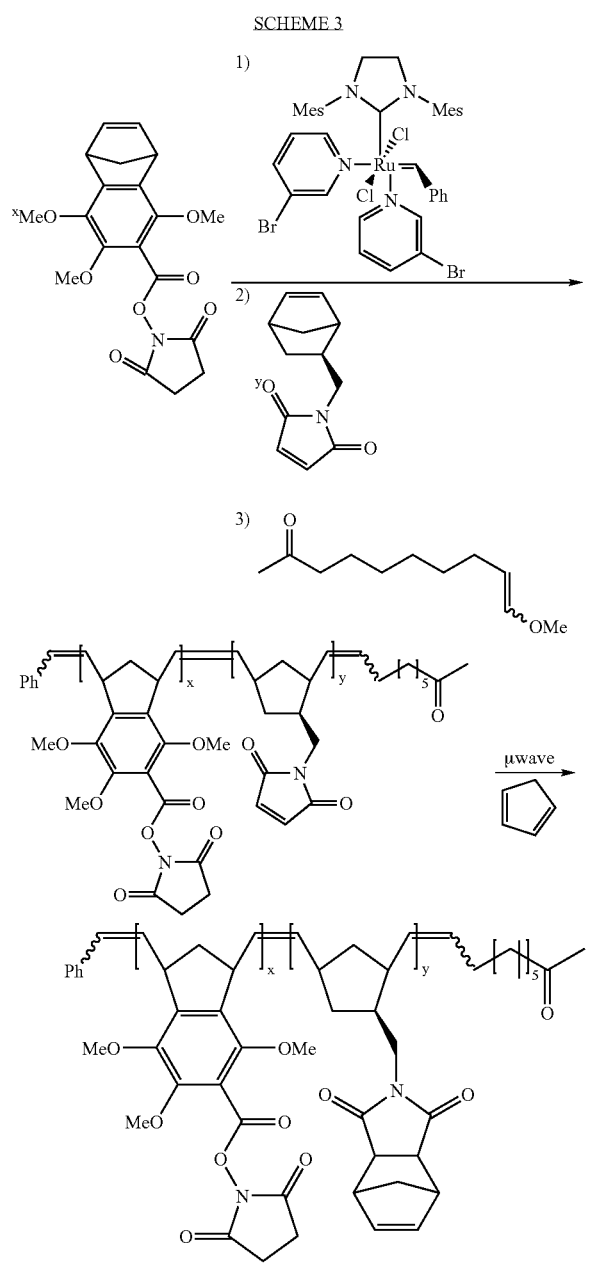

THE EXAMPLES

Example 1

General Experimental Procedures

Commercial chemicals were of reagent grade or better and used without further purification unless otherwise noted. Dichloromethane and diisopropylethylamine were distilled from calcium hydride; tetrahydrofuran (THF) was distilled from sodium/benzophenone, and methanol was distilled from magnesium.

Flash chromatography was performed using silica gel 60, 230-450 mesh (Sorbent Technologies). Analytical thin-layer chromatography (TLC) was carried out on EM Science TLC plates precoated with silica gel 60 $F_{254}$ (250-μm layer thickness). TLC visualization was accomplished using a UV lamp and/or charring with potassium permanganate stain (3 g $KMnO_4$, 20 g $K_2CO_3$, 5 mL 5% (w/v) aqueous NaOH, 300 mL $H_2O$). MilliQ water and PD-10 columns (Amersham Biosciences) were used for polymer purification.

$^1$H NMR spectra were obtained using a Bruker AC-300 (300 MHz) or Varian UNITY-500 (500 MHz) spectrometer, and $^{13}$C NMR spectra were obtained using a Bruker AC-300 (75 MHz) spectrometer. Chemical shifts are reported relative to residual solvent signals ($CDCl_3$: $^1$H: δ 7.27, $^{13}$C: δ 77.23; $CD_3OD$: $^1$H: δ 3.31, $^{13}$C: δ 49.15; DMSO-$d_6$: $^1$H: δ 2.50, $^{13}$C: δ 39.51; $D_2O$: $^1$H: δ 4.79, $^{13}$C: δ 39.51—internal DMSO-$d_6$ standard). $^1$H NMR data are assumed to be first order with apparent doublets and triplets reported as d and t, respectively. Multiplets are reported as m, and resonances that appear broad are designated as bs. High-resolution electrospray ionization mass spectra (HRESI-MS) were obtained on a Micromass LCT. Liquid chromatography and mass spectrometry (LC-MS) analysis was performed on a Shimadzu LC-MS containing a C18 column (Supelco Discovery, 2.1× 150 mm) equilibrated with 0.4% (v/v) formic acid.

Polydispersity index (PDI) values were obtained using a Beckman Coulter high-performance liquid chromatography system, two Polymer Laboratories PLgel 5 μm MIXED-D 300×7.5 mm columns in series, Polymer laboratories EasiCal Polystyrene Standards (PS-1), and Cirrus GPC offline GPC/SEC Software Version 1.2. Elemental analyses and Gd solution concentration determinations were performed at Desert Analytics Laboratory, Tucson, Ariz.

The longitudinal water proton relaxation rate at 60 MHz was measured by using a Bruker mq60 NMR Analyzer (Bruker Canada, Milton, Ont. Canada) operating at 1.5 T, by means of the standard inversion-recovery technique (20 data points, 8 scans each). A typical 90°-pulse length was 6.16 μs, and the reproducibility of the $T_1$ data was ±0.3%. Temperature was maintained at 22° C. with a Haake G cooling circulator.

3-Hydroxy-6-methyl-2-oxo-1,2-dihydropyridine-4-carboxylic acid ethyl ester (4) (Doble, D. M. J.; Melchoir, M.; O'Sullivan, B.; Siering, C.; Xu, J.; Pierre, V. C.; Raymond, K. N. Inorg. Chem. 2003, 42, 4930-4937), 10-methoxydec-9-en-2-one (Pontrello, J. K.; Allen, M. J.; Underbakke, E. S.; Kiessling, L. L. J. Am. Chem. Soc. 2005, 127, 14536-14537), and $(H_2IMes)(3-Br-py)_2(Cl)_2Ru=CHPh$ (Love, J. A.; Morgan, J. P. Trnka, T. M.; Grubbs, R. H. Angew. Chem., Int. Ed. 2002, 41, 4035-4037) were synthesized following the previously described procedures.

Example 2

Synthesis of 5,7,8-Trimethoxy-1,4-dihydro-1,4-methanonaphthalene-6-carboxylic acid 2,5-dioxopyrrolidin-1-yl ester (3)

Compound 3 was prepared as illustrated in the following scheme:

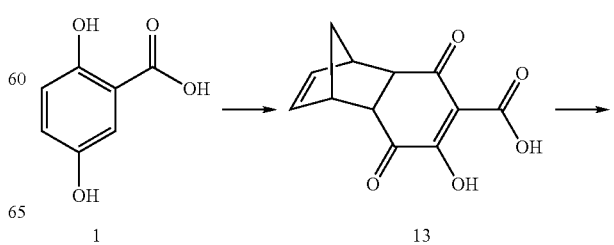

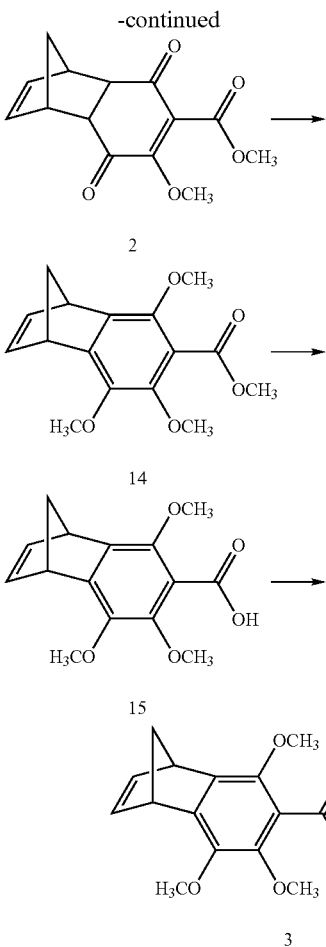

7-Hydroxy-5,8-dioxo-1,4,4α,5,8,8α-hexahydro-1,4-methanonaphthalene-6-carboxylic acid (13)

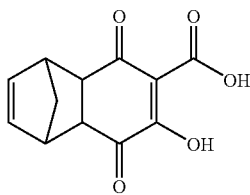

Modifications to a previously described procedure were used (Holmes, T. J.; Vennerstrom, V. J. J.; Choi, K. E. *J. Org. Chem.* 1984, 49, 4736-4738).

A suspension of 2,5-dihydroxybenzoic acid (40.0 g, 0.263 mol) and ammonium cerium(IV) sulfate (315 g, 0.528 mol) in carbon tetrachloride (3 L) was mechanically stirred rapidly in the dark for 45 min. The suspension was filtered, and freshly cracked cyclopentadiene (50 mL, 0.61 mmol) was added to the filtrate, and the mixture was allowed to stir. The solution color immediately changed from dark to light yellow. After 10 min, the solvent was removed under reduced pressure. The resulting orange solid was washed with hexanes, dissolved in dichloromethane, and concentrated three times to yield 2.79 g (4.5%) of 13 as an orange solid. Formation of 13 only occurred with new bottles of carbon tetrachloride; distilled carbon tetrachloride did not yield the desired product. $^1$H NMR (300 MHz, CDCl$_3$): δ=1.55-1.69 (m, 2H, CH$_2$), 3.32-3.36 (m, 1H, (CH)$_2$—CH—CH$_2$), 3.53-3.57 (m, 1H, (CH)$_2$—CH—CH$_2$), 3.63-3.68 (m, 2H, (CH)$_2$—CH—C(O)), 6.10-6.17 (m, 2H, HC=CH, 14.19 (bs, 1H, OH), 15.12 (bs, 1H, C(O)OH; $^{13}$C NMR (75 MHz, CDCl$_3$): δ=47.0 ((CH)$_2$—CH—CH$_2$), 47.6 ((CH)$_2$—CH—CH$_2$), 49.5 (CH$_2$), 49.6 ((CH)$_2$—CH—C(O)), 50.1 ((CH)$_2$—CH—C(O)), 107.3 ((C(O))$_2$—C=C), 135.5 (HC=CH), 135.9 (HC=CH), 173.4, 175.5, 193.2, 199.2; ESI-MS calcd for C$_{12}$H$_{10}$O$_5$ [M–H]$^-$: 233.0450. found 233.0457.

7-Methoxy-5,8-dioxo-1,4,4α,5,8,8α-hexahydro-1,4-methanonaphthalene-6-carboxylic acid methyl ester (2):

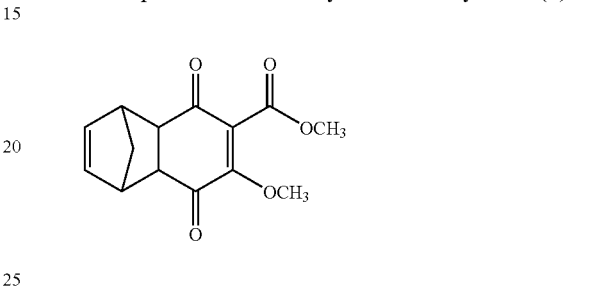

To a cooled (0° C.), stirred mixture of aqueous 50% KOH (100 mL) and diethyl ether (200 mL) was added nitrosomethyl urea (17.6 g, 171 mmol). When the ether layer turned yellow, it was decanted into an Erlenmeyer flask containing KOH pellets at 0° C. The ether layer was then decanted into an ether solution (200 mL) of 13 (2.00 g, 8.54 mmol) at 0° C. After 30 min, the reaction mixture was warmed to ambient temperature and stirred for 1 h. Purification was performed using silica gel chromatography (dichloromethane) to yield 1.89 g (85%) of 3 as a sticky yellow solid. $^1$H NMR (300 MHz, CDCl$_3$): δ=1.41-1.57 (m, 2H, CH$_2$), 3.21-3.31 (m, 2H, (CH)$_2$—CH—CH$_2$), 3.51-3.54 (m, 2H, (CH)$_2$—CH—C(O)), 3.83 (s, 3H, CO—CH$_3$), 3.96 (s, 3H, C(O)O—CH$_3$), 6.07-6.18 (m, 2H, HC=CH); $^{13}$C NMR (75 MHz, CDCl$_3$): δ=48.8 ((CH)$_2$—CH—CH$_2$), 49.0 ((CH)$_2$—CH—CH$_2$), 49.0 (CH$_2$), 49.2 ((CH)$_2$—CH—C(O)), 49.4 ((CH)$_2$—CH—C(O)), 52.9 (CO—CH$_3$), 59.8 (C(O)O—CH$_3$), 135.0 (HC=CH), 136.1 (HC=CH), 158.9, 164.7, 194.8, 195.4; ESI-MS calcd for C$_{14}$H$_{14}$O$_5$ [M+H]$^+$: 263.0919. found 263.0929.

5,7,8-Trimethoxy-1,4-dihydro-1,4-methanonaphthalene-6-carboxylic acid methyl ester (14)

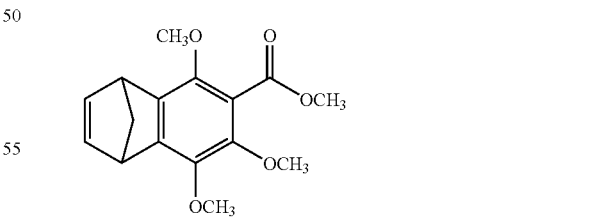

To a refluxing solution of 2 (2.50 g, 9.53 mmol) in acetone (60 mL) was added dimethyl sulfate (9.0 mL, 95 mmol). A 10% methanolic KOH solution was added dropwise until the color of the solution stopped changing from purple to tan. The reaction mixture was heated at reflux for 1 h, at which point a 2 N HCl solution was added until the mixture turned clear. The reaction mixture was extracted four times with dichloromethane, dried over sodium sulfate, and concentrated. Purification was performed using silica gel chromatography (1:4 ethyl acetate/hexanes) to yield 1.86 g (67%) of 14 as a yellow oil. $^1$H NMR (300 MHz, CDCl$_3$): δ=2.15-2.23 (m, 2H, CH$_2$), 3.83 (s, 3H, O—CH$_3$), 3.83 (s, 3H, O—CH$_3$), 3.85 (s, 3H, O—CH$_3$), 3.90 (s, 3H, CO$_2$—CH$_3$), 4.16-4.18 (m, 2H, CH—CH(C)—CH$_2$), 6.76-6.82 (m, 2H, HC=CH); $^{13}$C NMR (75 MHz, CDCl$_3$): δ=47.6 (CH—CH(C)—CH$_2$), 48.0 (CH—CH(C)—CH$_2$), 52.5 (CO$_2$—CH$_3$), 61.6 (O—CH$_3$), 61.9 (O—CH$_3$), 62.2 (O—CH$_3$), 68.5 (CH$_2$), 119.2, 137.2, 142.5 (HC=CH), 142.8 (HC=CH), 144.0, 146.6, 146.8, 147.9, 167.0; TLC: R$_f$=0.67 (2:1 ethyl acetate/hexanes); ESI-MS calcd for C$_{16}$H$_{18}$O$_5$ [M+Na]$^+$: 313.1052. found 313.1037.

5,7,8-Trimethoxy-1,4-dihydro-1,4-methanonaphthalene-6-carboxylic acid (15)

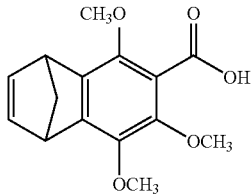

To a solution of 14 (0.591 g, 2.05 mmol) in methanol (50 mL) was added a 4 N NaOH solution (50 mL), and the resulting reaction mixture was heated at reflux for 5 h. Methanol was removed under reduced pressure and a 3 N HCl solution was added to achieve pH 1. The reaction mixture was extracted three times with ethyl acetate, dried over sodium sulfate, and concentrated under reduced pressure to yield 0.567 g of 15 as a brown oil in nearly quantitative yield. $^1$H NMR (300 MHz, CDCl$_3$): δ=2.18-2.27 (m, 2H, CH$_2$), 3.86 (s, 3H, O—CH$_3$), 3.89 (s, 3H, O—CH$_3$), 3.92 (s, 3H, O—CH$_3$), 4.19-4.22 (m, 2H, CH—CH(C)—CH$_2$), 6.78-6.86 (m, 2H, HC=CH); $^{13}$C NMR (75 MHz, CDCl$_3$): δ=47.6 (CH—CH(C)—CH$_2$), 47.9 (CH—CH(C)—CH$_2$), 61.6 (CH$_3$), 62.1 (CH$_3$), 62.5 (CH$_3$), 68.5 (CH$_2$), 117.9, 137.8, 142.4 (HC=CH), 142.9 (HC=CH), 144.2, 147.2, 147.6, 148.6, 170.6; ESI-MS calcd for C$_{15}$H$_{16}$O$_5$ [M–H]$^-$: 275.0920. found 275.0910.

5,7,8-Trimethoxy-1,4-dihydro-1,4-methanonaphthalene-6-carboxylic acid 2,5-dioxopyrrolidin-1-yl ester (3)

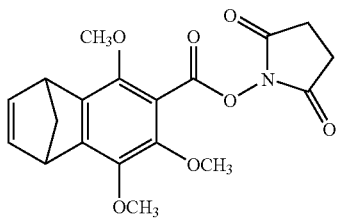

To a solution of 15 (0.972 g, 3.52 mmol) in dichloromethane (80 mL) was added N-hydroxysuccinimide (0.547 g, 4.75 mmol) and 1-[3-(dimethylamino)propyl]-3-ethylcarbodiimide hydrochloride (0.890 g, 4.64 mmol), and the resulting reaction mixture was stirred under dinitrogen for 15 h. The reaction mixture was diluted with dichloromethane (100 mL), washed twice with a 0.01 N HCl solution (50 mL), dried over sodium sulfate, and concentrated under reduced pressure. Purification was performed using silica gel chromatography (dichloromethane→2:1 ethyl acetate/hexanes) to yield 0.898 g (68%) of 3 as a colorless sticky solid. $^1$H NMR (300 MHz, CDCl$_3$): δ=2.19-2.27 (m, 2H, CH—CH$_2$—CH), 2.89 (bs, 4H, CH$_2$—CH$_2$), 3.86 (s, 3H, O—CH$_3$), 3.92 (s, 3H, O—CH$_3$), 3.95 (s, 3H, O—CH$_3$), 4.19-4.23 (m, 2H, CH—CH(C)—CH$_2$), 6.78-6.85 (m, 2H, HC=CH); $^{13}$C NMR (75 MHz, CDCl$_3$): δ=25.9 (CH$_2$—CH$_2$), 47.7 (CH—CH(C)—CH$_2$), 47.9 (CH—CH(C)—CH$_2$), 61.7 (O—CH$_3$), 62.3 (O—CH$_3$), 62.6 (O—CH$_3$), 68.6 (CH—CH$_2$—CH), 137.7, 142.4 (CH=CH), 143.0 (CH=CH), 144.2, 147.9, 149.6, 149.9, 161.4, 169.1; TLC: R$_f$=0.42 (2:1 ethyl acetate/hexanes); ESI-MS calcd for C$_{19}$H$_{19}$NO$_7$ [M+Na]$^+$: 396.1059. found 396.1069.

Example 3

Synthesis of Compound 7

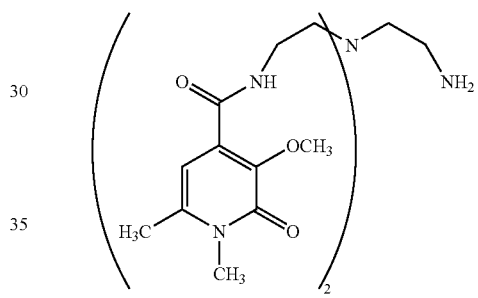

Compound 7 was prepared as illustrated in the following scheme:

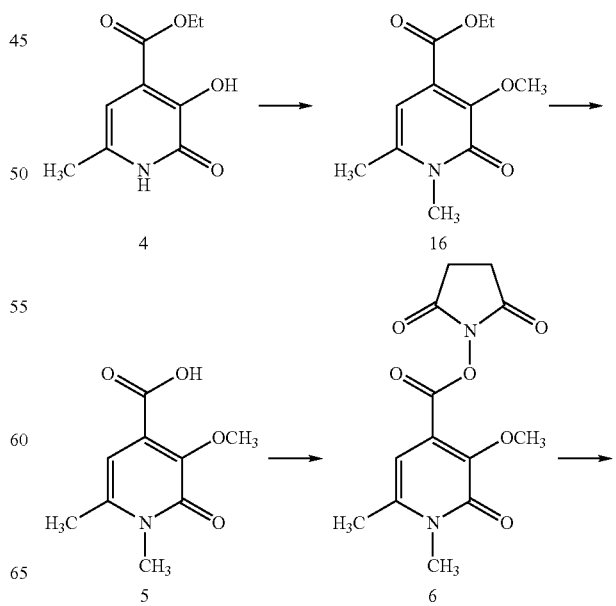

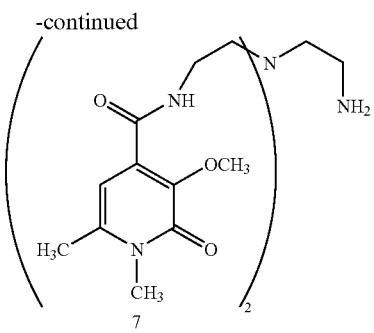

(7)

3-Methoxy-1,6-dimethyl-2-oxo-1,2-dihydropyridine-4-carboxylic acid ethyl ester (16)

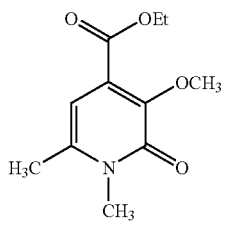

To a solution of 4 (8.69 g, 44.1 mmol) in dimethylformamide (440 mL) was added potassium carbonate (12.7 g, 91.6 mmol) and methyl iodide (27.5 mL, 441 mmol), and the resulting reaction mixture was stirred for 15 h. The reaction was concentrated under reduced pressure and diluted with dichloromethane (200 mL) and water (200 mL). The layers were separated, and the aqueous layer was extracted with dichloromethane (50 mL). The combined organic layers were dried over sodium sulfate and concentrated under reduced pressure. Purification was performed using silica gel chromatography (2:1 ethyl acetate/hexanes) to yield 7.89 g (80%) of 16 as a tan solid. $^1$H NMR (300 MHz, CDCl$_3$): δ=1.36 (t, 3H, J=7.1 Hz, CH$_2$—CH$_3$), 2.32 (s, 3H, C—CH$_3$), 3.52 (s, 3H, N—CH$_3$), 3.94 (s, 3H, O—CH$_3$), 4.33 (q, 2H, J=7.1 Hz, CH$_2$), 6.16 (s, 1H, CH); $^{13}$C NMR (75 MHz, CDCl$_3$): δ=14.3 (CH$_2$—CH$_3$), 20.7 (C—CH$_3$), 31.9 (N—CH$_3$), 60.4 (O—CH$_3$), 61.7 (CH$_2$), 103.8 (CH), 129.5, 140.3, 146.4, 160.7, 165.4; TLC: R$_f$=0.20 (2:1 ethyl acetate/hexanes); ESI-MS calcd for C$_{11}$H$_{15}$NO$_4$ [M+H]$^+$: 226.1079. found 226.1072.

3-Methoxy-1,6-dimethyl-2-oxo-1,2-dihydropyridine-4-carboxylic acid (5)

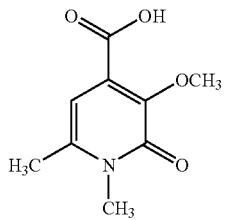

To a solution of 16 (7.51 g, 33.3 mmol) in methanol (350 mL) was added a 4 M sodium hydroxide solution (350 mL).

The resulting solution was heated at reflux, and after 2 h, methanol was removed under reduced pressure. An aqueous 3 N HCl solution was used to adjust the resulting solution to pH 1. The solution was extracted with ethyl acetate; the organic extracts were dried over sodium sulfate, and solvent was removed under reduced pressure to yield 6.44 g (98%) of 5 as a tan solid. $^1$H NMR (300 MHz, CD$_3$OD): δ=2.40 (s, 3H, C—CH$_3$), 3.58 (s, 3H, N—CH$_3$), 3.86 (s, 3H, O—CH$_3$), 6.36 (s, 1H, CH); $^{13}$C NMR (75 MHz, CD$_3$OD): δ=20.6 (C—CH$_3$), 32.6 (N—CH$_3$), 61.0 (O—CH$_3$), 105.9 (CH), 132.8, 143.4, 146.6, 162.6, 168.2; ESI-MS calcd for C$_9$H$_{11}$NO$_4$ [M−H]$^−$: 196.0610. found 196.0615.

3-Methoxy-1,6-dimethyl-2-oxo-1,2-dihydropyridine-4-carboxylic acid 2,5-dioxopyrrolidin-1-yl ester (6)

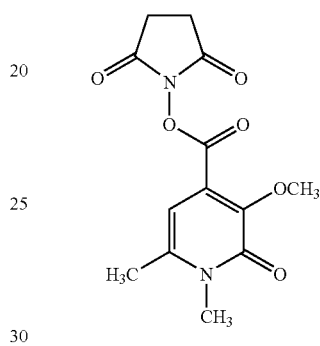

To a solution of 5 (5.36 g, 27.2 mmol) in dichloromethane (500 mL) was added N-hydroxysuccinimide (4.23 g, 36.7 mmol) and 1-[3-(dimethylamino)propyl]-3-ethylcarbodiimide hydrochloride (6.89 g, 35.9 mmol), and the resulting reaction mixture was stirred under dinitrogen for 15 h. The reaction mixture was washed twice with a 0.01 N HCl solution (150 mL), dried over sodium sulfate, and concentrated under reduced pressure. Purification was performed using silica gel chromatography (1:49 methanol/dichloromethane) to yield 7.83 g (98%) of 6 as a tan solid. $^1$H NMR (300 MHz, CDCl$_3$): δ=2.31 (s, 3H, C—CH$_3$), 4.08 (s, 4H, CH$_2$), 3.50 (s, 3H, N—CH$_3$), 3.98 (s, 3H, O—CH$_3$), 6.29 (s, 1H, CH); $^{13}$C NMR (75 MHz, CDCl$_3$): δ=20.6 (C—CH$_3$), 25.8 (CH$_2$), 32.0 (N—CH$_3$), 60.8 (O—CH$_3$), 103.0 (CH), 122.8, 140.7, 148.8, 159.9, 160.3, 169.0; TLC: R$_f$=0.33 (1:19 methanol/dichloromethane); ESI-MS calcd for C$_{13}$H$_{14}$N$_2$O$_6$ [M+H]$^+$: 295.0930. found 295.0931.

Compound 7:

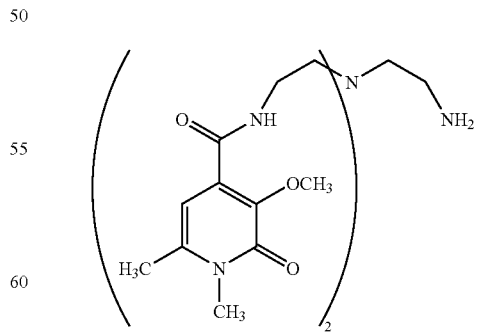

Tritylchloride resin (2.0 g, 3.2 mmol) was swelled in tetrahydrofuran (20 mL) for 15 min at which point tris(2-aminoethyl)amine (4.98 mL, 32.0 mmol) was added, and the resulting solution was mixed for 20 h. The resin was drained and washed four times with 20 mL of 17:2:1 dichloromethane/methanol/diisopropylethylamine, and three times with 20 mL of dichloromethane. To the washed resin was added dichloromethane (20 mL), diisopropylethylamine (5.57 mL, 32.0 mmol), and 6 (3.77 g, 12.8 mmol), and the resulting solution was stirred for 20 h. The resin was drained and washed three times with 20 mL of dichloromethane and dried under reduced pressure. A solution of 38:1:1 trifluoroacetic acid/triisopropylsilane/water (24 mL) was added to the resin; after 2 h, the resin was filtered and rinsed with trifluoroacetic acid (5 mL). The combined trifluoroacetic acid-containing filtrate was reduced in volume to 2 mL. This solution was added dropwise to diethyl ether (400 mL) at 0° C., and the resulting precipitate was collected. Purification was performed using basic alumina chromatography (1:9→3:7 methanol/dichloromethane) to yield 1.0 g (63%) of 7 as a white solid. $^1$H NMR (300 MHz, CD$_3$OD): δ=2.39 (s, 6H, C—CH$_3$), 2.62-2.78 (m, 8H, H$_2$N—CH$_2$ and N—(CH$_2$)$_3$), 3.48 (t, 4H, J=6.2 Hz, C(O)NH—CH$_2$), 3.56 (s, 6H, N—CH$_3$), 3.88 (s, 6H, O—CH$_3$), 6.40 (s, 2H, CH); $^{13}$C NMR (75 MHz, CD$_3$OD): δ=20.7 (C—CH$_3$), 32.6 (N—CH$_3$), 39.1 (C(O)NH—CH$_2$), 40.3 (H$_2$N—CH$_2$), 54.5 (N—(CH$_2$)$_3$), 57.7 (N—(CH$_2$)$_3$), 60.9 (O—CH$_3$), 105.7 (CH), 133.3, 143.3, 145.5, 161.9, 166.4; TLC: R$_f$=0.21 (1:19 methanol/dichloromethane on basic alumina plates); ESI-MS calcd for C$_{24}$H$_{36}$N$_6$O$_6$ [M+H]$^+$: 505.2775. found 505.2794.

Example 4

Polymerization Reactions

Polymerization was carried out as illustrated in the following scheme:

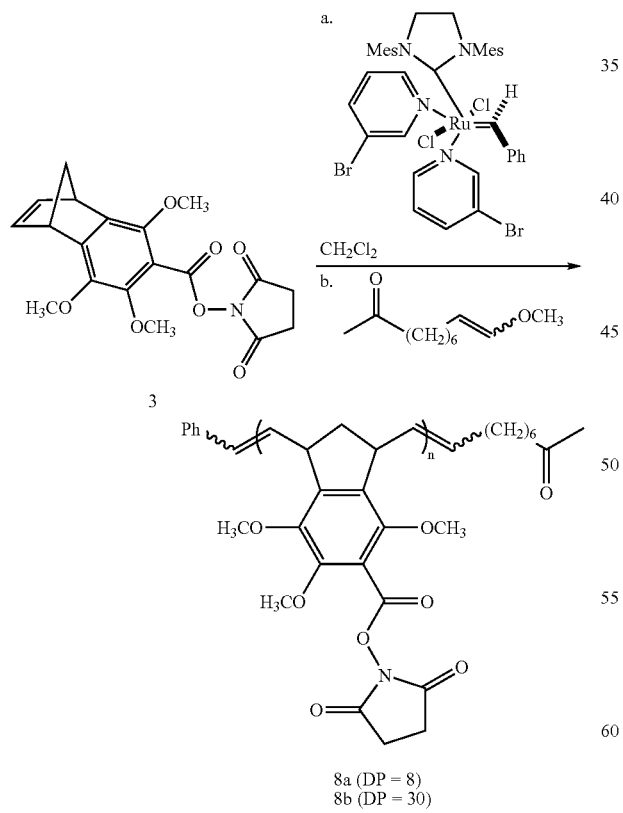

Polymerizations were carried out under an argon atmosphere in scintillation vials. Solutions of (H$_2$IMes)(3-Br-py)$_2$(Cl)$_2$Ru=CHPh (5.35 mM) and 3 (0.134 M) in degassed dichloromethane were cooled to −20° C. The solutions were combined in the desired monomer to initiator ratio, and degassed dichloromethane was added to bring the final concentration of 3 to 38.3 mM. The reactions were allowed to warm slowly to ambient temperature. After consumption of 3, as determined by TLC, 10-methoxydec-9-en-2-one (20 μL, 0.10 mmol) was added, and the reaction mixture was allowed to stir for 15 h. The reaction mixtures were added dropwise to a 30-fold volume excess of diethyl ether. The resulting white solid was collected, and residual solvent was removed under reduced pressure.

For Polymer 8a:

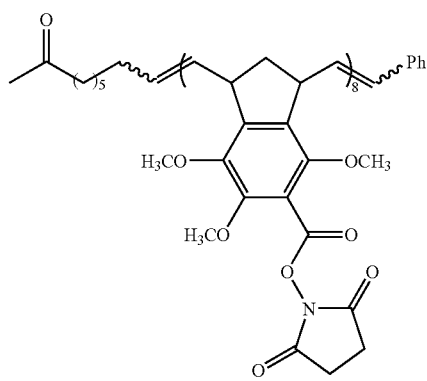

Yield=76.3 mg (71%) black solid. $^1$H NMR (500 MHz, DMSO-d$_6$): δ=1.53 (bs), 2.50 (bs), 2.86 (bs, C(=O)—CH$_2$—CH$_2$—C(=O)), 3.73 (bs, O—CH$_3$), 4.24 (bs), 5.52 (bs, 18H, HC=CH), 7.14 (bs, 5H, C$_6$H$_5$); PDI 1.58; Calculated MW 3217; M$_w$ 2788; M$_n$ 1760.

For Polymer 8b:

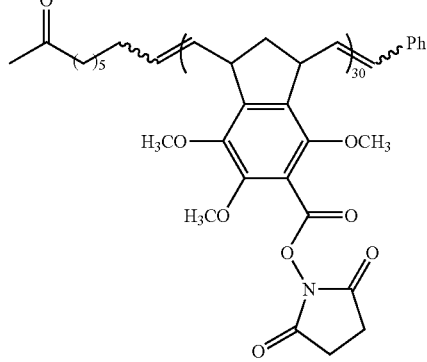

Yield=165 mg (94%) off-white solid. $^1$H NMR (500 MHz, DMSO-d$_6$): δ=1.07 (bs), 2.84 (bs, C(=O)—CH$_2$—CH$_2$—C(=O)), 3.64 (bs, O—CH$_3$), 5.31 (bs, 63H, HC=CH), 7.00 (bs, 5H, C$_6$H$_5$); PDI 1.21; Calculated MW 11431; M$_w$ 5004; M$_n$ 4122.

Example 5

General Procedure for Conjugation of Polymers with Compounds 7 and 14

Conjugation were carried out as illustrated in the following scheme:

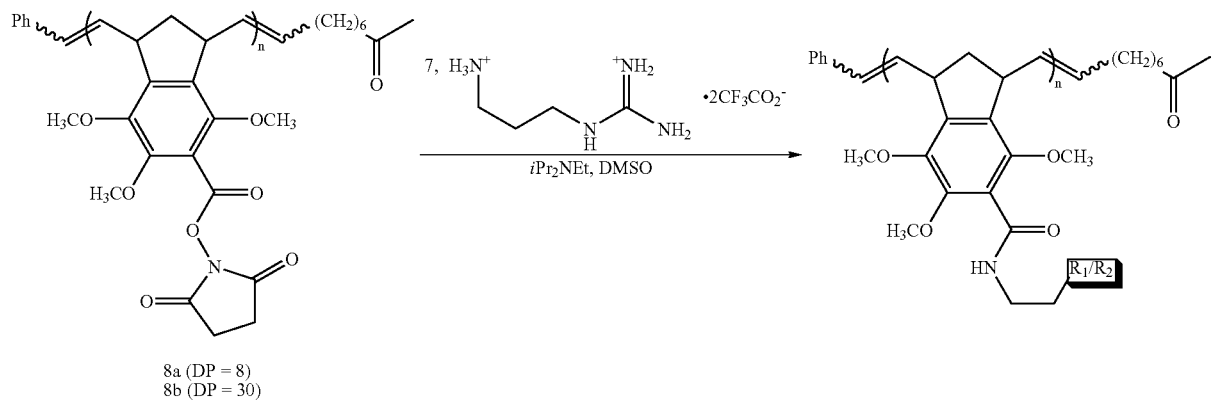

8a (DP = 8)
8b (DP = 30)

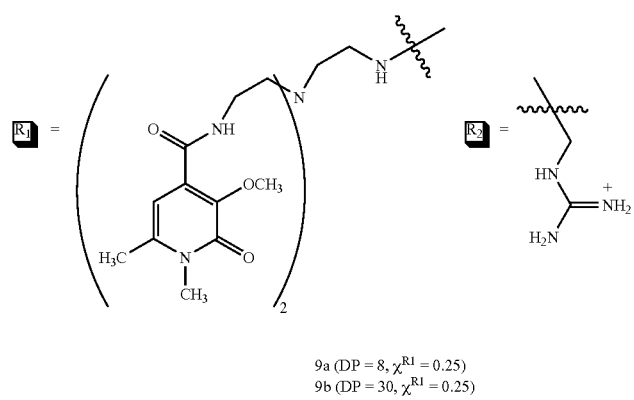

9a (DP = 8, $\chi^{R1} = 0.25$)
9b (DP = 30, $\chi^{R1} = 0.25$)

To a solution of polymer 8a or 8b (5 mg) in dimethylsulfoxide (200 μL) and diisopropylethylamine (10 equivalents per monomer unit) was added 7 (0.25 equivalents per monomer unit) and N-(3-aminopropyl)guanidine bis-trifluoroacetic acid salt (0.75 equivalents per monomer unit). After 15 h, the entire reaction mixture was passed through a PD-10 column. Fractions containing polymer were collected, and solvent was removed under reduced pressure.

For Polymer 9a:

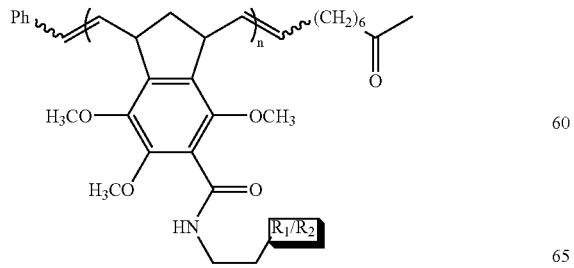

-continued

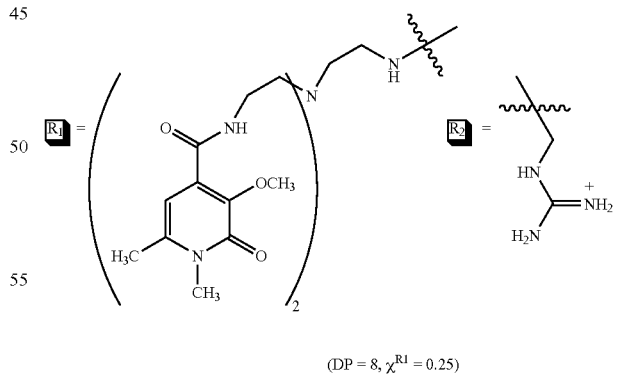

(DP = 8, $\chi^{R1} = 0.25$)

Yield=12.4 mg (70%) brown solid. $^1$H NMR (500 MHz, DMSO-$d_6$): δ=1.18 (bs), 1.68 (bs), 2.31 (bs), 2.65 (bs), 3.20 (bs), 3.43 (bs), 3.68 (bs), 4.12 (bs), 5.42 (bs, 17H, HC=CH), 6.22 (bs, 2.9H, C—CH=C—CH$_3$), 7.20 (bs), 7.69 (bs), 8.31 (bs).

For Polymer 9b:

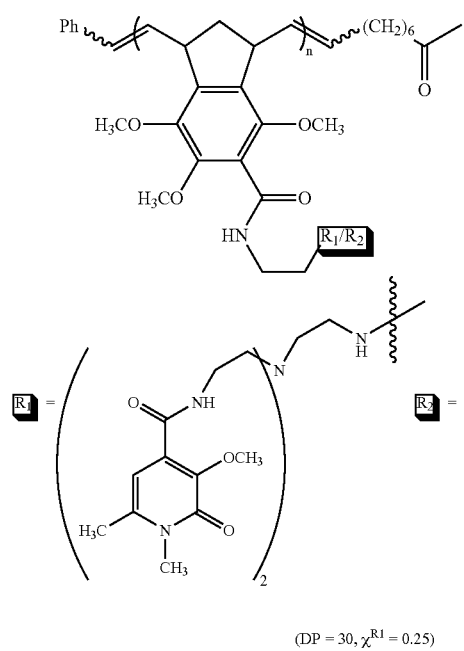

(DP = 30, χ^R1 = 0.25)

Yield=8.37 mg (38%) brown glass. $^1$H NMR (500 MHz, DMSO-d$_6$): δ=1.18 (bs), 1.68 (bs), 2.31 (bs), 2.65 (bs), 3.20 (bs), 3.43 (bs), 3.68 (bs), 4.12 (bs), 5.42 (bs, 62H, HC=CH), 6.22 (bs, 7.6H, C—CH=C—CH$_3$), 7.20 (bs), 7.69 (bs), 8.31 (bs).

Example 6

Synthesis of Compound 12

Compound 12 was synthesized as illustrated in the following scheme:

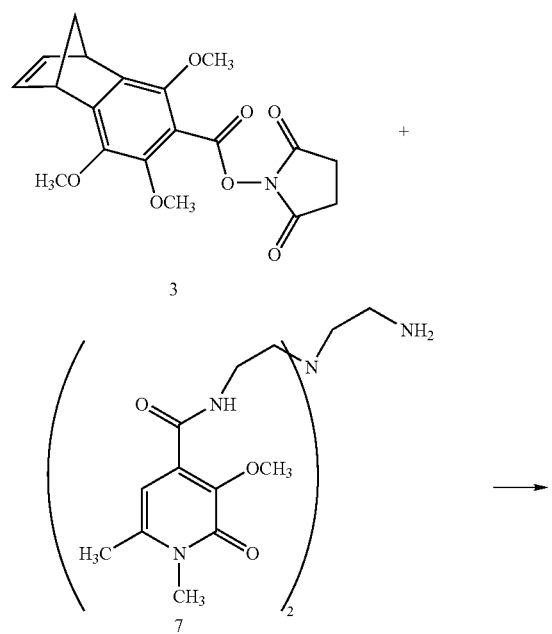

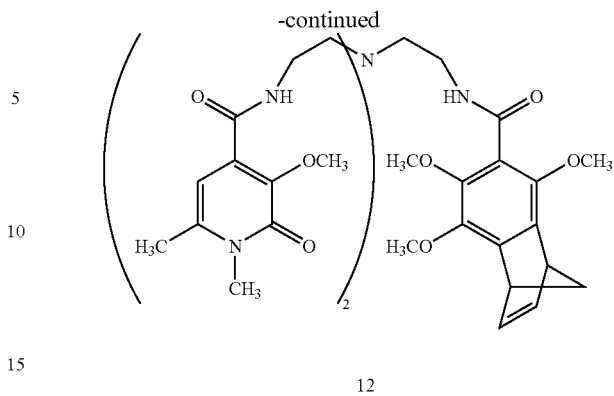

12

A solution of 7 (0.304 g, 0.603 mmol), 3 (0.150 g, 0.402 mmol), and diisopropylethylamine (0.350 mL, 2.01 mmol) in dichloromethane (10 mL) was stirred under dinitrogen for 4 h, at which point solvent was removed under reduced pressure. Purification was performed using silica gel chromatography (1:19 methanol/dichloromethane) to yield 0.202 g (66%) of 12 as a white solid. $^1$H NMR (300 MHz, CDCl$_3$): δ=2.10-2.20 (m, 2H, CH—CH$_2$—CH), 2.33 (s, 6H, C—CH$_3$), 2.79-2.86 (m, 6H, N—(CH$_2$)$_3$), 3.49-3.55 (m, 12H, C(O)NH—CH$_2$ and N—CH$_3$), 3.80 (s, 3H, O—CH$_3$), 3.81 (s, 3H, O—CH$_3$), 3.82 (s, 3H, O—CH$_3$), 3.94 (s, 6H, O=C—C(=C)—O—CH$_3$), 4.11-4.14 (m, 2H, CH—CH (C)—CH$_2$), 6.27-6.31 (t, 1H, J=5.6 Hz, (CH$_3$—O—C)$_2$—C—C(=O)—NH), 6.55 (s, 2H, CH$_3$—C=CH—C), 6.73-6.78 (m, 2H, CH=CH), 8.16-8.20 (t, 2H, J=5.2 Hz, CH—C—C(=O)—NH); $^{13}$C NMR (75 MHz, CDCl$_3$): δ=20.8 (C—CH$_3$), 31.9 (N—CH$_3$), 38.2 (C(O)NH—CH$_2$), 47.6 (CH—CH(C)—CH$_2$), 47.9 (CH—CH(C)—CH$_2$), 53.7 (N—(CH$_2$)$_3$), 53.8 (N—(CH$_2$)$_3$), 60.0 (O=C—C(=C)—O—CH$_3$), 61.6 (O—CH$_3$), 62.1 (O—CH$_3$), 62.4 (O—CH$_3$), 68.4 (CH—CH$_2$—CH), 104.5 (CH$_3$—C=CH—C), 122.3, 129.3, 137.4, 140.2, 142.4 (CH=CH), 142.9 (CH=CH), 144.2, 145.1, 145.7, 146.9, 147.7, 160.2, 163.9, 166.2; TLC: R$_f$=0.26 (2:23 methanol/dichloromethane); ESI-MS calcd for C$_{39}$H$_{50}$N$_6$O$_{10}$ [M+H]$^+$: 763.3667. found 763.3648.

Example 7

Deprotection of Methyl Ethers and Metallation

To a solution of methyl ether-protected chelate (1 eq. of 9a, 9b, or 12) in anhydrous dimethylsulfoxide (DMSO) under argon was added a solution of sodium ethanethiolate (2.5 eq. per OMe) in anhydrous DMSO to make a final solution of between 0.4 and 26 mM chelate and between 44 and 328 mM sodium ethanethiolate. The resulting solution was heated to 142° C. for 1.5 h at which point a four-fold volume excess of water was added to quench excess sodium ethanethiolate. The reaction mixture was concentrated to dryness under reduced pressure, and LC-MS of the product resulting from 12 showed one major product with a mass corresponding to four of five methyl ethers removed.

To ensure that the remaining methoxy group was not in a position to interfere with metal chelation, a portion of the intermediate (0.80 mg, 1.2 μmol) was dissolved in anhydrous DMSO (11.4 μL) under argon. To the resulting solution was added CH$_2$I$_2$ (1.4 μmol, 0.11 μL) and sodium carbonate (2.5 μmol, 0.27 mg), and the reaction was heated to 55° C. for 8 h, as illustrated below. The mixture was cooled to ambient temperature, and 2 mL of water was added. LC/MS indicated that there was one major product with mass ([M+H]$^+$=721.4) corresponding to the formation of a methylene bridge between the two ortho hydroxyl groups. This result indicates that the remaining methoxy group was not in a position to interfere with metal chelation. Additional support for the position of the remaining methoxy group is found in the work of Feutrill and Mirrington (Feutrill, G. I.; Mirrington, R. N. *Tetrahedron Lett.* 1970, 16, 1327-1328). They treated a series of anisole compounds with sodium ethanethiolate and found that ortho-methoxy groups underwent complete demethylation while para-methoxy groups yielded selective mono-demethylation.

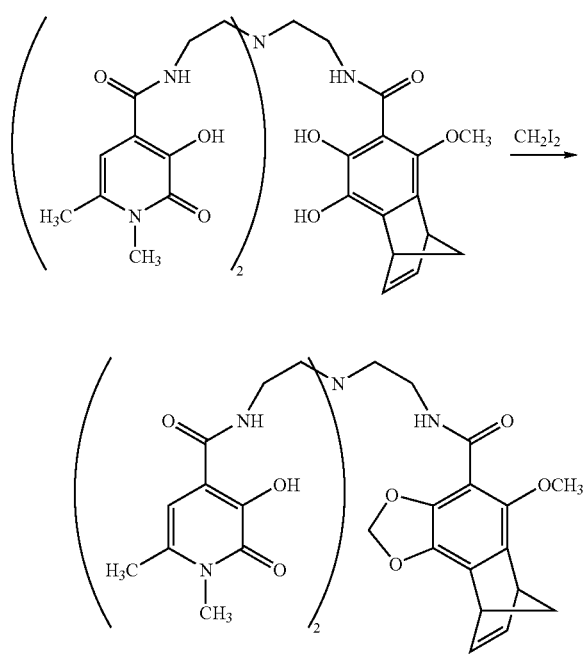

The intermediate was dissolved in water in a concentration between 0.1 and 6.5 mM, and five drops of DMSO were added. One equivalent of GdCl$_3$.6H$_2$O per chelating group was then added, and the pH of the resulting solution was adjusted to 7 using 0.1 N NaOH and 0.1 N HCl solutions. The reaction mixture was heated to 80° C. for 1 h, at which point the pH was readjusted to 7. The reaction mixture was allowed to sit at ambient temperate for 15 h. The pH was brought to 10 using a 0.1 N NaOH solution to precipitate any unchelated gadolinium as Gd(OH)$_3$. Gd(OH)$_3$ was removed by filtration through a 0.45 µm syringe filter. The pH of the filtered solution was brought to 7 using a 0.1 N HCl solution, and the resulting solution was directly used for T$_1$ acquisition. After measurement of T$_1$, solutions were analyzed for Gd concentration, and the T$_1$ and Gd concentration data were used to calculate per Gd relaxivity. Per Gd relaxivity was multiplied by the number of chelates per polymer (as determined by NMR spectroscopy of polymers 9) to determine molecular relaxivity values.

The Intermediate of methyl ether removal from 12 is:

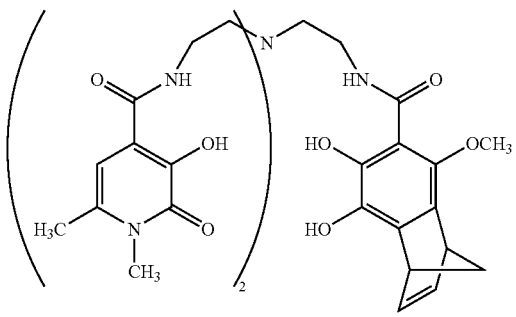

ESI-MS calcd for C$_{35}$H$_{42}$N$_6$O$_{10}$ [M+H]$^+$: 707.3. found 707.4.

The Gd complex 11 is:

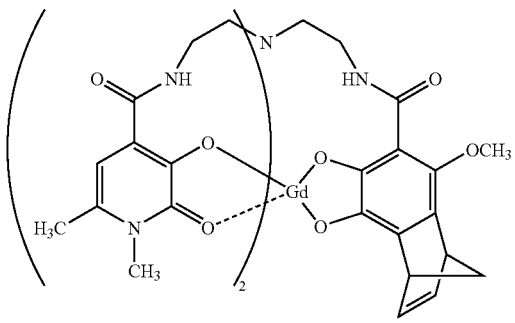

ESI-MS calcd for C$_{35}$H$_{38}$GdN$_6$O$_{10}$ [M–CH$_3$+Na+2H]$^+$: Gd isotope pattern centered at 870.2, found Gd isotope pattern centered at 870.1. Maximum Gd concentrations ranged from 0.0054% to 0.0176%. Relaxivity (r$_1$): 10.5±0.8 mM$^{-1}$ s$^{-1}$ (error is given as the standard deviation).

Polymer 10a is:

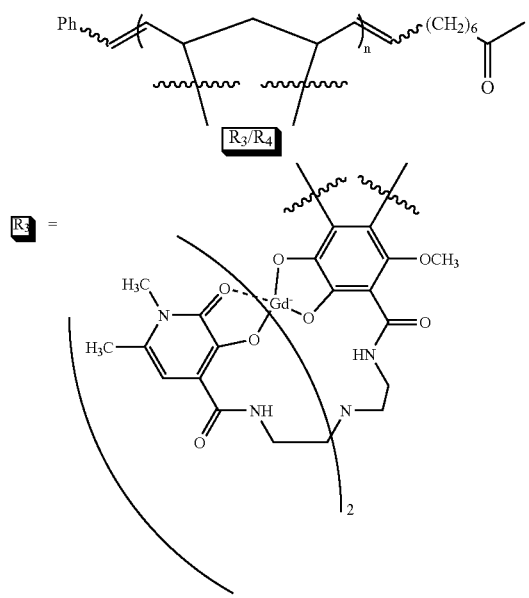

-continued

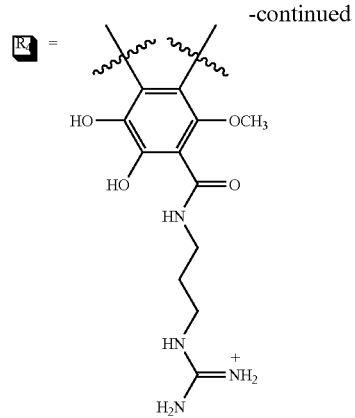

(DP = 8, $\chi^{R3}$ = 0.25)

$\chi^{R3}$=0.25, $\chi^{R4}$=0.75. Maximum Gd concentrations ranged from 0.0040% to 0.0046%. Ionic relaxivity ($r_1$): 10.1±0.5 mM$^{-1}$ s$^{-1}$; Molecular relaxivity ($r_1$): 18.8±0.9 mM$^{-1}$ s$^{-1}$ (errors are given as standard deviations).

Polymer 10b is:

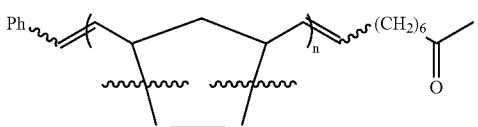

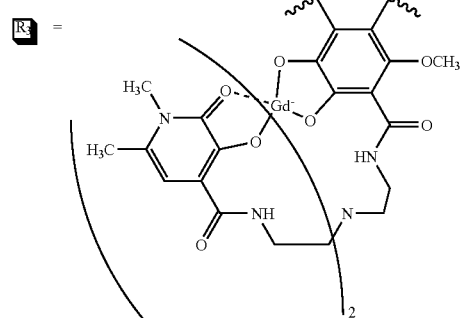

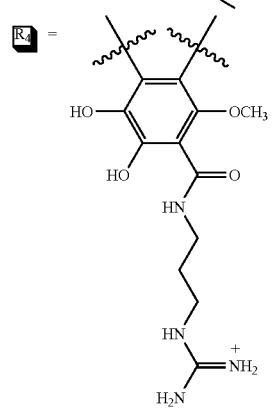

(DP = 30, $\chi^{R3}$ = 0.25)

$\chi^{R3}$=0.25, $\chi^{R4}$=0.75. Maximum Gd concentrations ranged from 0.0005% to 0.0048%. Ionic relaxivity ($r_1$): 14.8±0.2 mM$^{-1}$ s$^{-1}$; Molecular relaxivity ($r_1$): 111.0±1.5 mM$^{-1}$ s$^{-1}$ (errors are given as standard deviations).

Example 8

Preparation of Bis-Trifluoroacetic Acid Salts

N-(3-aminopropyl)guanidine bis-trifluoroacetic acid salt:

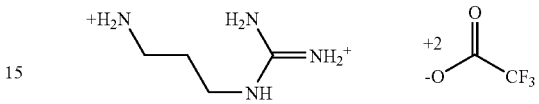

N-(bis-Boc-guanyl)-N-Boc-1,3-diaminopropane (1.00 g, 2.40 mmol) was dissolved in 20 mL of 95% trifluoroacetic acid (TFA), 2.5% water, and 2.5% triisopropylsilane (v/v/v). After 14 h, the volume was reduced to a sticky residue under a stream of air. The residue was washed with diethyl ether, dissolved in water, and freeze dried to yield 0.568 g (69%) of the desired salt as an extremely viscous, colorless oil. $^1$H NMR (300 MHz, D$_2$O): δ=1.96-2.06 (m, 2H, CH$_2$—CH$_2$—CH$_2$), 3.11 (t, 2H, J=8.0 Hz, N—CH$_2$—CH$_2$), 3.35 (t, 2H, J=7.0 Hz, N—CH$_2$—CH$_2$); $^{13}$C NMR (75 MHz, D$_2$O): δ=27.6 (CH$_2$—CH$_2$—CH$_2$), 38.3 (N—CH$_2$), 39.7 (N—CH$_2$), 158.3 (C—(N)$_3$); ESI-MS calcd for C$_4$H$_{12}$N$_4$ [2M+H]$^+$: 233.3. found 233.1; Anal. Calcd for C$_8$H$_{14}$F$_6$N$_4$O$_4$: C, 27.91; H, 4.10; F, 33.12; N, 16.28. Found: C, 27.87; H, 4.24; F, 31.17; N, 15.55.

Example 9

Preparation of N-(bis-Boc-guanyl)-N'-Boc-1,3-diaminopropane

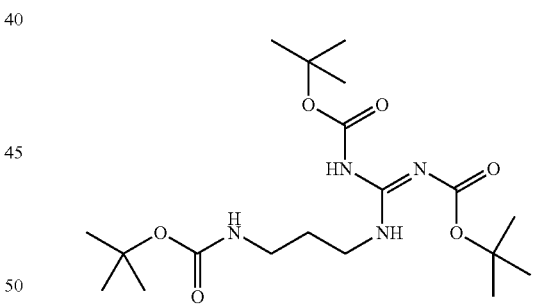

To a solution of N-Boc-1,3-diaminopropane (5.00 mL, 28.6 mmol) in dimethylformamide (DMF) (100 mL) was added diisopropylethylamine (DIEA) (3.72 mL, 21.4 mmol) and bis-Boc-guanylpyrazole (3.31 g, 10.7 mmol). The reaction mixture was stirred for 14 h, at which time DMF was removed under reduced pressure. Water (20 mL) was added, and the mixture was extracted with dichloromethane. The organic layer was dried over magnesium sulfate, and solvent was removed under reduced pressure. Purification was performed using silica gel chromatography (5:1→2:1 hexanes/ethyl acetate) to yield 3.07 g (69%) of the desired product as a white solid. $^1$H NMR (300 MHz, CDCl$_3$): δ=1.43 (s, 9H, CH$_3$), 1.49 (s, 18H, CH$_3$), 1.64-1.72 (m, 2H, CH$_2$—CH$_2$CH$_2$), 3.10-3.17 (m, 2H, NH—CH$_2$—CH$_2$), 3.44-3.50 (m, 2H, NH—CH$_2$—CH$_2$), 5.60 (s, 1H, NH), 8.34 (t, 1H, J=5.6 Hz, NH), 11.41 (s, 1H, NH); $^{13}$C NMR (75 MHz, CDCl$_3$): δ=28.3 (CH$_3$), 28.5 (CH$_3$), 28.7 (CH$_3$), 30.4 (CH$_2$—CH$_2$—CH$_2$), 37.3 (NH—CH$_2$—CH$_2$), 37.8 (NH—CH$_2$—CH$_2$), 79.0 (C(CH$_3$)$_3$), 79.4 (C(CH$_3$)$_3$), 83.4 (C(CH$_3$)$_3$), 153.4, 156.4, 156.9, 163.5; TLC: R$_f$=0.36 (2:1 hexanes/ethyl acetate); ESI-MS calcd for C$_{19}$H$_{36}$N$_4$O$_6$ [M+H]$^+$: 417.2713. found 417.2693.

Example 10

Estimation of Rotational Correlation Time

Values of the rotational correlation time ($\tau_R$) were estimated using the Debye-Stokes equation shown below and data acquired for other linear Gd$^{III}$ containing polymers (Toth, E.; Helm, L.; Kellar, K. E.; Merbach, A. E. *Chem. Eur. J.* 1999, 5, 1202-1211; *The Chemistry of Contrast Agents in Medical Magnetic Resonance Imaging*; Merbach, A. E., Toth, E., Eds.; John Wiley & Sons, Ltd.: New York, 2001). Assuming that the microviscosity and density of the polymers are the same, the ratio of molecular radii can be expressed by the ratio of the molecular weights. While the Debye-Stokes equation provides estimation for spherical molecules, the ROMP-derived polymers and polymers in the above references are both linear and the ratio of their molecular weights is used only as an approximation.

$$\tau_R = \frac{4\pi\eta r_{eff}^3}{3k_B T}$$

Debye-Stokes equation (η=microviscosity, r$_{eff}$=molecular radius, k$_B$=the Boltzmann constant, T=temperature)

Table 1 below shows average molecular weight (MW), $\tau_R$, and per Gd relaxivity for two linear polymers from the literature ($\tau_g$, global motion correlation time, was used to estimate $\tau_R$ for comparison to ROMP-derived polymers 10a and 10b because of the rigid connection to the polymer backbone). The $\tau_R$ data for ROMP-derived polymers 10a and 10b were estimated by plotting $\tau_R$ vs. MW for the published polymers, and using the resulting slope with the molecular weights of polymers 10a and 10b. The ratio of $\tau_R$ to relaxivity was then examined, and the relaxivity values in parentheses for 10a and 10b would be expected for linear polymers with their molecular weights and estimated $\tau_R$ values. These estimates match up very well with the actual measurements indicating that there is relaxivity increase due to increase in $\tau_R$. Thus, the observed increase is proportional to what is seen in linear polymers of Gd$^{III}$ diethylenetriaminepentaacetic acid (DTPA).

TABLE 1

| Polymer | MW (Da) | $\tau_R$ (10$^{-12}$ s) | Relaxivity Per Gd relaxivity (mM$^{-1}$s$^{-1}$) |
|---|---|---|---|
| [DTPA-BA(CH$_2$)$_{10}$]$_x$ | 10300 | 2900 | 15.4 |
| [DTPA-BA(CH$_2$)$_{12}$]$_x$ | 15700 | 4400 | 19.6 |
| 10a | 4260 | 1200 | 10.1 (10.7) |
| 10b | 14200 | 4000 | 14.8 (18.5) |

Additional experimental details of the synthesis and analysis of polymers useful as contrast agents may be found in Allen M. J., Raines, R. T. and Kiessling, L. L. (2006) *J. Amer. Chem. Soc.* 128(20):6534-6536 and supporting information thereof, each of which is incorporated by reference in its entirety herein.

We claim:

1. A metal chelating polymer having formula:

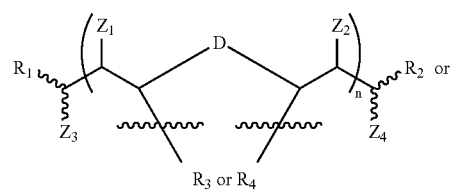

and salts thereof, where:

n indicates the average number of repeating units in the polymer and where the degree of polymerization (DP) ranges from 8-100;

D is selected from C(R$_a$)$_2$, O, S, NR$_N$, or NCOR$_N$;

each Z$_1$-Z$_4$, independently, is hydrogen or a hydroxyl group;

R1 and R$_2$ are independently selected from hydrogen, aryl, ketone, aldehyde, or a -L$_4$-R$_{10}$ group, where R$_{10}$ is selected from a reactive functional group, a targeting group, a labeling group, a particle, or a solid and L$_4$ is a linker;

R$_3$ is a metal chelating group with or without a metal ion chelated in the chelating group, wherein R$_3$ has the formula:

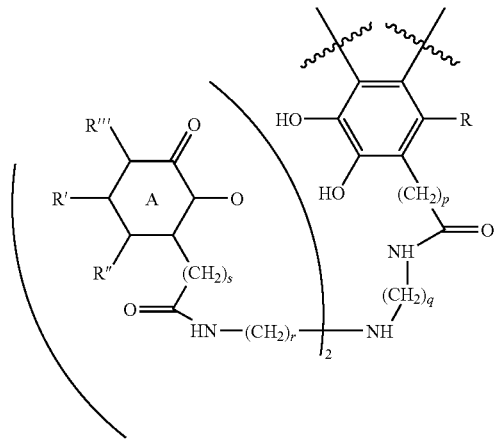

where the A ring is selected from:

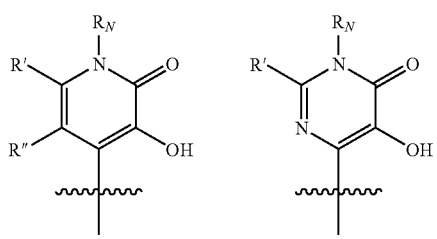

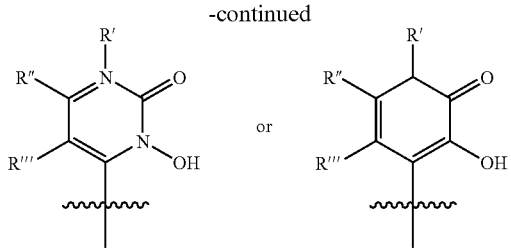

p and s are independently 0, 1, 2, or 3;
q and r are independently 1, 2, or 3;
R, R', R", R'" are independently selected from the group consisting of hydrogen, halide, alkyl, alkenyl, alkynyl, aryl, alkoxy, aryloxy, thioalkoxy, ether, thioether, heterocyclic, hydroxyl, carboxyl, ester, amino, and amide groups, each of which is optionally substituted with one or more substituents selected from halide, amine, hydroxyl, alkyl, alkenyl, alkynyl, aryl, alkoxy, or aryloxy groups;
$R_N$ is selected from the group consisting of hydrogen, alkyl, alkenyl, alkynyl, ether, amine, amide, ester, and aryl groups, wherein one or more carbons of these groups is optionally substituted with one or more substituents selected from halide, hydroxyl, alkyl, alkoxy, aryl, or aryloxy groups; and
R4 is a group other than a chelating group selected from a spacer group, a reactive functional group, a targeting group, a solubilizing group, a labeling group, an $R_M$ group, where $R_M$ is a group which carries a cyclic olefin group which reacts by ROMP, or a ROMP polymer side branch formed by ROMP polymerization from the $R_M$ group; wherein the metal chelating polymer contains at least one $R_3$ group and optionally contains multiple different $R_4$ groups.

2. The metal chelating polymer of claim 1 wherein $Z_1$ and $Z_2$ are hydrogens.

3. The metal chelating polymer of claim 2 wherein $Z_3$ and $Z_4$ are hydrogens.

4. The metal chelating polymer of claim 1 wherein $Z_1$ and $Z_2$ are hydroxyl groups.

5. The metal chelating polymer of claim 4 wherein $Z_3$ and $Z_4$ are hydroxyl groups.

6. The metal chelating polymer of claim 1 wherein D is —$CH_2$— or —O—.

7. The metal chelating polymer of claim 1 wherein the $R_4$ groups are spacer groups having the formula:

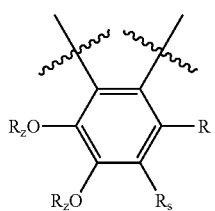

where:
$R_z$ is independently selected from a hydrogen, a protecting group that can be removed or an alkyl group having 1 to 6 carbon atoms;
$R_s$ is independently selected from:
alkyl, alkenyl, alkynyl, aryl, alkoxy, aryloxy, thioalkoxy, ether, thioether, or heterocyclic groups, in which one or more non-neighboring carbons are optionally replaced with —O—, —S—, —$NR_N$—, —CO—, —COO—, or —$CONR_N$— and which are optionally substituted with one or more substituents selected from halide, amine, hydroxyl, alkyl, alkenyl, alkynyl, aryl, alkoxy, aryloxy, —$N^+(R_N)_3$, —NH—C(=$NH_2$)$^+$—$NH_2$, —$COO^-$, or a -$L_3$-$R_5$ group, where $L_3$ is a linker group and $R_5$ is selected from a reactive functional group, a targeting group, a macromolecule, a particle, a solid or a labeling group.

8. The metal chelating polymer of claim 7 wherein only one or two of the $R_4$ groups of the polymer have $R_s$ groups which are -$L_3$-$R_5$ groups.

9. The metal chelating polymer of claim 1 which chelates one or more metal ions which is an ion of a transition metal, an actinide metal, or a lanthanide metal.

10. The metal chelating polymer of claim 9 wherein the metal is a metal in the +3 oxidation state.

11. The metal chelating polymer of claim 10 wherein the metal is Gd(III).

12. A metal chelating polymer of claim 1 having the formula:

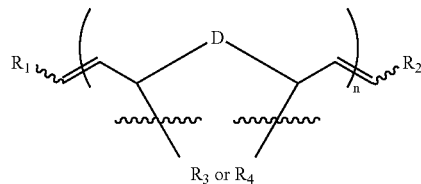

and salts thereof.

13. A contrast agent for diagnostic imaging comprising a polymer of claim 1 which chelates at least one metal.

14. The contrast agent of claim 13, which includes a targeting moiety which allows the contrast agent to target a selected biological component.

15. The contrast agent of claim 14, wherein the targeting moiety is selected from the group consisting of lipophilic substances, receptor ligands, and antibodies.

16. A method of performing contrast enhanced magnetic resonance imaging on a patient, comprising:
administering to the patient an amount of a compound of claim 1 effective to enhance the contrast; and acquiring a magnetic resonance imaging data set from the patient.

17. The metal chelating polymer of claim 1 wherein $R_4$ groups are spacer groups having the formula:

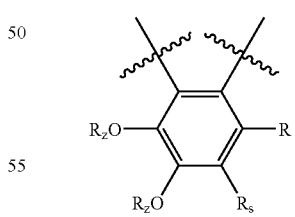

where:
$R_z$ is independently selected from a hydrogen, a protecting group that can be removed or an alkyl group having 1 to 6 carbon atoms;
$R_s$ is independently selected from alkyl, alkenyl, alkynyl, aryl, alkoxy, aryloxy, thioakoxy, ether, thioether, or heterocyclic groups in which one or more non-neighboring carbons are optionally replaced with —O—, —S—, —$NR_N$—, —CO—, —COO—, or —$CONR_N$— and which are optionally substituted with one or more —N⁺(R$_N$)$_3$, —NH—C(=NH$_2$)⁺—NH$_2$, or —COO⁻ groups or salts thereof.

18. The metal chelating polymer of claim 1 wherein R$_3$ has the formula:

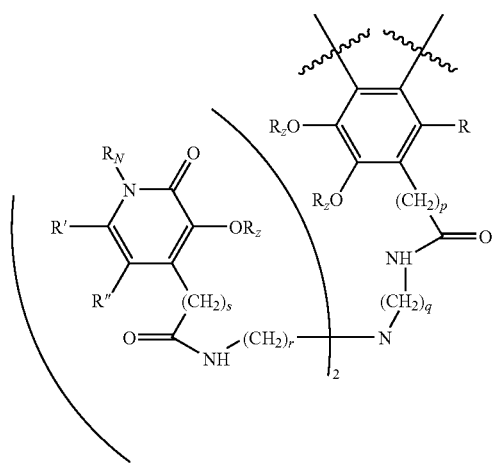

where p and s are independently 0, 1, 2, or 3; and q and r are independently 1, 2, or 3.

19. The metal chelating polymer of claim 1 wherein R$_3$ has the formula:

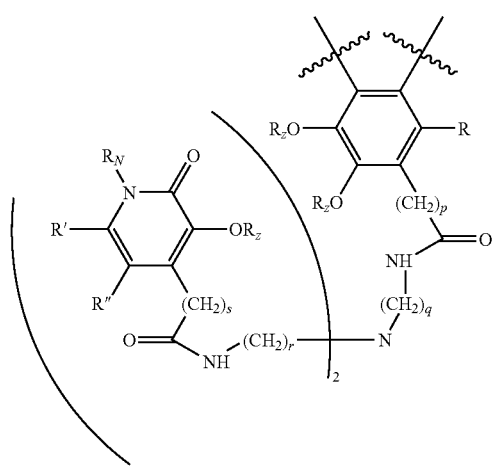

where p and s are independently 0, 1, 2, or 3; and q and r are independently 1, 2, or 3.

20. The metal chelating polymer of claim 19 wherein M is Gd(III).

21. The metal chelating polymer of claim 1 wherein R, R', R" and R'" are independently selected from the group consisting of alkyl, alkoxy, aryl, aryloxy and amine groups, which are optionally substituted with one or more halide, hydroxyl, alkyl or aryl groups; and R$_N$ is selected from the group consisting of hydrogen, alkyl, alkenyl, alkynyl, ether, amine, amide, ester and aryl groups, wherein one or more carbons of these groups are optionally substituted with one or more halide, hydroxyl, alkyl, alkoxy, aryl or aryloxy groups.

22. The metal chelating polymer of claim 1 wherein DP ranges from 10-50.

23. The metal chelating polymer of claim 1 wherein:

R$_{10}$ is selected from an activated ester; a fluorophore; a radioactive label; a hydrophilic or charged group; a peptide, nucleic acid, receptor ligand, sugar or antigen; a particle or a solid; and R$_4$ is selected from an activated ester; a fluorophore; a radioactive label; a hydrophilic or charged group; a peptide, nucleic acid, receptor ligand, sugar or antigen; a particle or a solid; or a spacer group having the formula:

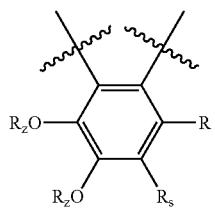

where:

R is independently selected from hydrogen, halide, hydroxyl, alkyl or alkoxy;

R$_z$ is independently selected from a hydrogen, a protecting group that can be removed or an alkyl group having 1 to 6 carbon atoms; and R$_s$ is independently selected from alkyl, alkenyl, alkynyl, aryl, alkoxy, aryloxy, thioalkoxy, ether, thioether, or heterocyclic groups, in which one or more non-neighboring carbons are optionally replaced with —O—, —S—, —NR$_N$—, —CO—, —COO—, or —CONR$_N$— and which are optionally substituted with one or more substituents selected from halide, amine, hydroxyl, alkyl, alkenyl, alkynyl, aryl, alkoxy, aryloxy, —N⁺(R$_N$)$_3$, —NH—C(=NH$_2$)⁺—NH$_2$, —COO⁻, or a -L$_3$-R$_5$ group, where L$_3$ is a linker group and R$_5$ is selected from an activated ester; a fluorophore; a radioactive label; a hydrophilic or charged group; a peptide, nucleic acid, receptor ligand, sugar or antigen; a particle or a solid.

24. The metal chelating polymer of claim 1 wherein R$_4$ groups are spacer groups having the formula:

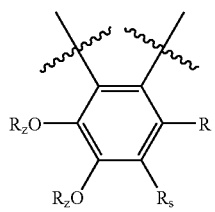

where:

R is independently selected from hydrogen, halide, hydroxyl, alkyl or alkoxy;

R$_z$ is independently selected from a hydrogen, a protecting group that can be removed or an alkyl group having 1 to 6 carbon atoms; and R$_s$ is an alkyl group in which one or more non-neighboring carbons can be replaced with —O—, —S—, —NR$_N$—, —CO—, —COO—, or —CONR$_N$— and which is optionally substituted with one or more —N⁺(R$_N$)$_3$, —NH—C(=NH$_2$)⁺—NH$_2$ or —COO⁻ groups or salts thereof.

25. The metal chelating polymer of claim 12 wherein $R_4$ groups are spacer groups having the formula:

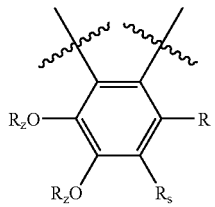

where:
R is independently selected from hydrogen, halide, hydroxyl, alkyl or alkoxy;
$R_z$ is independently selected from a hydrogen, a protecting group that can be removed or an alkyl group having 1 to 6 carbon atoms; and
$R_s$ is an alkyl group in which one or more non-neighboring carbons are optionally replaced with —O—, —S—, —$NR_N$—, —CO—, —COO—, or —$CONR_N$— and which is optionally substituted with one or more —$N^+(R_N)_3$, —NH—C($=NH_2$)$^+$—$NH_2$ or —COO$^-$ groups or salts thereof.

26. The metal chelating polymer of claim 25 wherein $R_1$ and $R_2$ are independently selected from a hydrogen, an aryl, a ketone, or an aldehyde group.

27. The metal chelating polymer of claim 25 where the A ring has the formula:

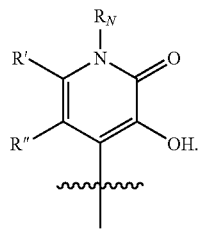

28. The metal chelating polymer of claim 27 wherein R, R', and R" are independently selected from the group consisting of hydrogen, alkyl, alkoxy, aryl and aryloxy, and $R_N$ is selected from hydrogen, alkyl or aryl groups wherein one or more carbons of the R, R', R" and $R_N$ groups is optionally substituted with one or more substituents selected from halide, hydroxyl, alkyl, alkoxy, aryl or aryloxy groups.

29. The metal chelating polymer of claim 28 wherein R, R', R" and $R_N$ are independently selected from the group consisting of hydrogen, and alkyl.

30. The metal chelating polymer of claim 27 wherein DP ranges from 20 to 40 and the ratio of spacer to chelating groups ranges from 5:1 to 2:1.

31. The metal chelating polymer of claim 25 wherein $R_4$ groups are spacer groups having the formula:

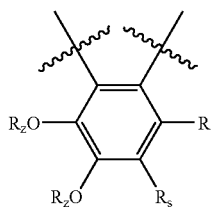

where $R_z$ is independently selected from a hydrogen, a protecting group that can be removed or an alkyl group having 1 to 6 carbon atoms; $R_s$ is an alkyl group in which one or more non-neighboring carbons are optionally replaced with —O—, —S—, —$NR_N$—, —CO—, —COO—, or —$CONR_N$— and which is optionally substituted with one or more —$N^+(R_N)_3$, —NH—C($=NH_2$)$^+$—$NH_2$, or —COO$^-$ groups or salts thereof.

32. The metal chelating polymer of claim 31 wherein the ratio of spacer groups to chelating groups ranges from 10:1 to 1:1.

33. The metal chelating polymer of claim 31 wherein DP ranges from 20 to 40 and the ratio of spacer to chelating groups ranges from 5:1 to 2:1.

34. The metal chelating polymer of claim 12 where the A ring has the formula:

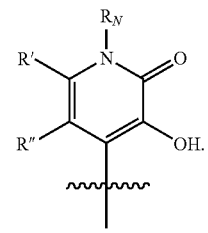

35. The metal chelating polymer of claim 34 wherein DP ranges from 20 to 40 and the ratio of spacer to chelating groups ranges from 5:1 to 2:1.

36. The metal chelating polymer of claim 12 wherein $R_1$ and $R_2$ are independently selected from a hydrogen, an aryl, a ketone, or an aldehyde group.

37. The metal chelating polymer of claim 1 wherein:
$R_1$ and $R_2$ are independently selected from a hydrogen, an aryl, a ketone, or an aldehyde group; and
$R_4$ is a spacer group having the formula:

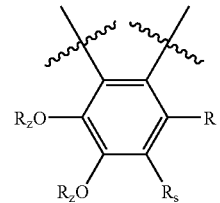

where:
$R_z$ is independently selected from a hydrogen, or an alkyl group having 1 to 6 carbon atoms; and
$R_s$ is independently selected from alkyl, alkenyl, alkynyl, aryl, alkoxy, aryloxy, thioalkoxy, ether, thioether, or heterocyclic groups, in which one or more non-neighboring carbons are optionally replaced with —O—, —S—, —$NR_N$—, —CO—, —COO—, or —$CONR_N$— and which are optionally substituted with one or more substituents selected from halide, amine, hydroxyl, alkyl, alkenyl, alkynyl, aryl, alkoxy, aryloxy, —$N^+(R_N)_3$, —NH—C($=NH_2$)$^+$—$NH_2$ or —COO$^-$.

38. The metal chelating polymer of claim 37 wherein:
the A ring has the formula:

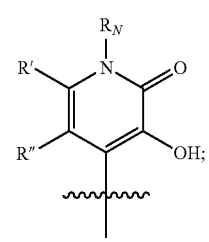

R, R', and R" are independently selected from the group consisting of hydrogen, halide, alkyl, alkoxy, thioalkoxy, ether, thioether, hydroxyl, carboxyl, ester, amino, and amide groups, each of which is optionally substituted with one or more substituents selected from halide, amine, hydroxyl, alkyl, alkenyl, alkynyl, or alkoxy groups; and $R_s$ is an alkyl group in which one or more non-neighboring carbons are optionally replaced with —O—, —S—, —$NR_N$—, —CO—, —COO—, or —$CONR_N$— and which is substituted with one or more —$N^+(R_N)_3$, —NH—C(=$NH_2$)$^+$—$NH_2$ or —COO$^-$ groups.

39. A contrast agent for diagnostic imaging comprising a polymer of claim 12 which chelates at least one metal.

40. A contrast agent for diagnostic imaging comprising a polymer of claim 18 which chelates at least one metal.

41. A graft copolymer comprising a polymer of claim 1.

* * * * *

UNITED STATES PATENT AND TRADEMARK OFFICE
CERTIFICATE OF CORRECTION

| | | |
|---|---|---|
| PATENT NO. | : 7,807,140 B2 | Page 1 of 1 |
| APPLICATION NO. | : 11/743740 | |
| DATED | : October 5, 2010 | |
| INVENTOR(S) | : Laura L. Kiessling et al. | |

It is certified that error appears in the above-identified patent and that said Letters Patent is hereby corrected as shown below:

In claim 1, column 50, line 3, after " 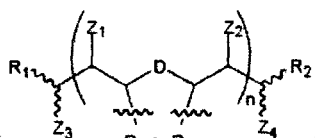 " please add

-- or 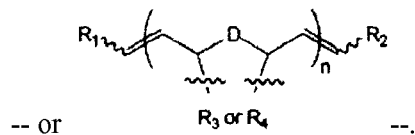 --.

In claim 1, column 50, line 25, please replace "R1" with -- $R_1$ --.

In claim 1, column 51, line 28, please replace "R4" with -- $R_4$ --.

In claim 19, column 53, line 20, please replace " 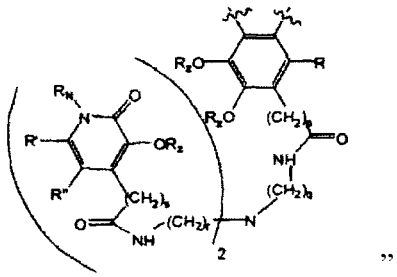 "

with -- 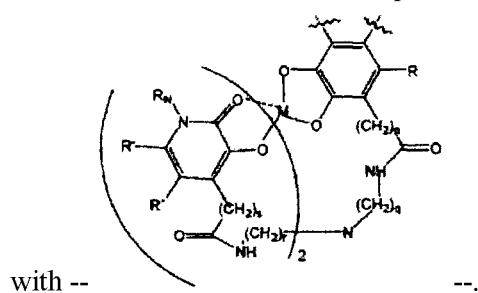 --.

Signed and Sealed this
Fourth Day of October, 2011

David J. Kappos
*Director of the United States Patent and Trademark Office*